(12) United States Patent
Martinell Pedemonte et al.

(10) Patent No.: US 11,957,670 B2
(45) Date of Patent: Apr. 16, 2024

(54) 5-[[4-[2-[5-(1-HYDROXYETHYL)PYRIDIN-2-YL]ETHOXY]PHENYL]METHYL]-1,3-THIAZOLIDINE-2,4-DIONE AND ITS SALTS FOR USE IN THE TREATMENT OF MITOCHONDRIAL DISEASES

(71) Applicant: Minoryx Therapeutics S.L., Barcelona (ES)

(72) Inventors: Marc Martinell Pedemonte, Barcelona (ES); Maria Pilar Pizcueta Lalanza, Barcelona (ES); Laura Pilar Rodríguez Pascau, Barcelona (ES)

(73) Assignee: Minoryx Therapeutics S.L., Mataró (ES)

(*) Notice: Subject to any disclaimer, the term of this patent is extended or adjusted under 35 U.S.C. 154(b) by 676 days.

(21) Appl. No.: 16/972,375

(22) PCT Filed: Jun. 6, 2019

(86) PCT No.: PCT/IB2019/054696
§ 371 (c)(1),
(2) Date: Dec. 4, 2020

(87) PCT Pub. No.: WO2019/234664
PCT Pub. Date: Dec. 12, 2019

(65) Prior Publication Data
US 2021/0228559 A1   Jul. 29, 2021

(30) Foreign Application Priority Data
Jun. 6, 2018  (EP) ...................................... 18382397

(51) Int. Cl.
*A61K 31/4439* (2006.01)
*A61K 9/00* (2006.01)
(Continued)

(52) U.S. Cl.
CPC ........ *A61K 31/4439* (2013.01); *A61K 9/0053* (2013.01); *A61P 21/00* (2018.01); *A61P 25/28* (2018.01); *A61P 27/02* (2018.01)

(58) Field of Classification Search
CPC ... A61K 31/4439; A61K 9/0053; A61P 21/00; A61P 25/28; A61P 27/02
See application file for complete search history.

(56) References Cited

U.S. PATENT DOCUMENTS 9,782,395 B2   10/2017  García Collazo et al.
10,179,126 B2   1/2019  García Collazo et al.
(Continued)

FOREIGN PATENT DOCUMENTS

JP   2016529224 A   9/2016
JP   2017014296 A   1/2017
(Continued)

OTHER PUBLICATIONS

Genetic Disorders by Cleveland Clinic, https://my.clevelandclinic.org/health/diseases/21751-genetic-disorders?view=print (Year: 2021).*
(Continued)

*Primary Examiner* — San Ming R Hui
(74) *Attorney, Agent, or Firm* — Sterne, Kessler, Goldstein & Fox P.L.L.C.

(57) ABSTRACT

The present disclosure relates to a method of treating or preventing mitochondrial diseases by administering 5-[[4-[2-[5-(1-hydroxyethyl)pyridin-2-yl]ethoxy]phenyl]methyl]-1,3-thiazolidine-2,4-dione or a salt thereof to a subject in need thereof. The disclosure also relates to 5-[[4-[2-[5-(1-hydroxyethyl)pyridin-2-yl]ethoxy]phenyl]methyl]-1,3-thiazolidine-2,4-dione for use in a pharmaceutical composition or in the manufacture of a medicament for the treatment or prevention of a mitochondrial disease.

18 Claims, 6 Drawing Sheets

(51) Int. Cl.
  *A61P 21/00*   (2006.01)
  *A61P 25/28*   (2006.01)
  *A61P 27/02*   (2006.01)

(56) References Cited

U.S. PATENT DOCUMENTS

| | | |
|---|---|---|
| 2016/0193231 A1 | 7/2016 | Scheer et al. |
| 2016/0331737 A1 | 11/2016 | Dewitt et al. |
| 2020/0093812 A1 | 3/2020 | Pizcueta Lalanza et al. |
| 2021/0228558 A1 | 7/2021 | Martinell Pedemonte et al. |
| 2021/0308113 A1 | 10/2021 | Martinell Pedemonte et al. |

FOREIGN PATENT DOCUMENTS

| | | |
|---|---|---|
| WO | WO-2012096873 A1 | 7/2012 |
| WO | WO-2015150476 A1 | 10/2015 |
| WO | WO-2017083739 A1 | 5/2017 |
| WO | WO-201800557 A1 | 6/2018 |
| WO | WO-2018116281 A1 | 6/2018 |

OTHER PUBLICATIONS

Abou-Samra, M., et al., "Involvement of adiponectin in the pathogenesis of dystrophinopathy," *Skeletal Muscle* 5:25, BioMed Central, United Kingdom (2015).

Bostick, B., et al., "Cardiac expression of a mini-dystrophin that normalizes skeletal muscle force only partially restores heart function in aged Mdx mice," *Molecular Therapy* 17(2):253-261, Cell Press, United States (2009).

Bostick, B., et al., "Prevention of Dystrophin-Deficient Cardiomyopathy in Twenty-One-Month-Old Carrier Mice by Mosaic Dystrophin Expression or Complementary Dystrophin/Utrophin Expression," *Circulation Research* 102:121-130, Lippincott Williams & Wilkins, United States (2008).

Colca, J.R., et al., "Identification of a Mitochondrial Target of Thiazolidinedione Insulin Sensitizers (mTOT)—Relationship to Newly Identified Mitochondrial Pyruvate Carrier Proteins," *PLOS ONE* 8(5):e61551, PLOS ONE, United States (2013).

Compan, V., et al., "Monitoring Mitochondrial Pyruvate Carrier Activity in Real Time Using a BRET-Based Biosensor: Investigation of the Warburg Effect," *Mol Cell*. 59:491-501, Cell Press, United States (2015).

Divakaruni, A.S., et al., "Inhibition of the mitochondrial pyruvate carrier protects from excitotoxic neuronal death," *J. Cell Biol*. 216(4): 1091-1105, Rockefeller University Press, United States (2017).

Divakaruni, A.S., et al., "Thiazolidinediones are acute, specific inhibitors of the mitochondrial pyruvate carrier," *PNAS* 110(14):5422-5427, National Academy of Sciences, United States (2013).

International Search Report and Written Opinion for International Application No. PCT/IB2019/054696, European Patent Office, Netherlands, dated Oct. 17, 2019, 12 pages.

Kamada, Y., et al., "Enhanced carbon tetrachloride-induced liver fibrosis in mice lacking adiponectin," *Gastroenterology* 125:1796-1807, Elsevier, United States (2003).

Koh, E., et al., "Essential role of mitochondrial function in adiponectin synthesis in adipocytes," *Diabetes* 56(12):2973-2981, American Diabetes Association, United States (2007).

Kus, V., et al., "Unmasking differential effects of rosiglitazone and pioglitazone in the combination treatment with n-3 fatty acids in mice fed a high-fat diet," *PLOS ONE* 6(11):e27156, PLOS ONE, United States (2011).

Maeshiba, Y., et al., "Disposition of the new antidiabetic agent pioglitazone in rats, dogs, and monkeys," *Arzneimittelforschung* 47(1):29-35, Thieme Medical Publishers, Germany (1997).

Mccommis, K.S., and Finck, B.N., "Mitochondrial pyruvate transport: a historical perspective and future research directions," *Biochem J*. 466(3):443-454, Biochemical Society, United Kingdom (2015).

Mccommis, K.S., et al., "Loss of Mitochondrial Pyruvate Carrier 2 in the Liver Leads to Defects in Gluconeogenesis and Compensation via Pyruvate-Alanine Cycling," *Cell Metab*. 22(4):682-694, Cell Press, United States (2015).

Mcgreevy, J., et al., "Animal models of Duchenne muscular dystrophy: from basic mechanisms to gene therapy," *Disease Models & Mechanisms* 8(3):195-213, Company of Biologists, United Kingdom (2015).

Niyazov, D.M., et al., "Primary Mitochondrial Disease and Secondary Mitochondrial Dysfunction: Importance of Distinction for Diagnosis and Treatment," *Mol Syndromol*. 7(3):122-137, Karger Publishers, Schwitzerland (2016).

Signorini, C., et al., "Redox Imbalance and Morphological Changes in Skin Fibroblasts in Typical Rett Syndrome," *Oxidative Medicine and Cellular Longevity* 2014:195935, Hindawi Publishing Corp., United Kingdom (2014).

Sohda, T., et al., "Studies on antidiabetic agents. XII. Synthesis and activity of the metabolites of (±)-5-[p-[2-(5-ethyl-2-pyridyl)ethoxy]benzyl]-2,4-thiazolidinedione (pioglitazone)," *Chem Pharm Bull* 43(12):2168-2172, Pharmaceutical Society of Japan, Japan (1995).

Zanou, N., et al., "Osmosensation in TRPV2 dominant negative expressing skeletal muscle fibres," *J. Physiol*. 593(17):3849-3863, Wiley-Blackwell, United States (2015).

De Filippis, B., et al., "Modulation of RhoGTPases improves the behavioral phenotype and reverses astrocytic deficits in a mouse model of Rett syndrome," Neuropsychopharmacology 37(5):1152-1163, Springer Nature, Germany (Apr. 2012).

Quintana, A., et al., "Complex I deficiency due to loss of Ndufs4 in the brain results in progressive encephalopathy resembling Leigh syndrome," Proc. Natl. Acad. Sci. USA 107(24):10996-11001, National Academy of Science, United States (Jun. 2010).

Quintana, A., et al., "Fatal breathing dysfunction in a mouse model of Leigh syndrome," J. Clin. Invest. 122(7):2359-2368, American Society for Clinical Investigation, United States (Jul. 2012).

\* cited by examiner

5-[[4-[2-[5-(1-HYDROXYETHYL)PYRIDIN-2-YL]ETHOXY]PHENYL]METHYL]-1,3-THIAZOLIDINE-2,4-DIONE AND ITS SALTS FOR USE IN THE TREATMENT OF MITOCHONDRIAL DISEASES

CROSS-REFERENCE TO RELATED APPLICATION

This application claims priority to European Application No. EP18382397.0, filed on Jun. 6, 2018, the entirety of which is incorporated by reference herein.

FIELD OF DISCLOSURE

The present disclosure relates to the use of 5-[[4-[2-[5-(1-hydroxyethyl)pyridin-2-yl]ethoxy]phenyl]methyl]-1,3-thiazolidine-2,4-dione and its pharmaceutically acceptable salts in the treatment or prevention of mitochondrial diseases.

BACKGROUND

Mitochondria are tiny subunits present inside every cell of the human body except red blood cells. Mitochondria's main role is to transform food and oxygen that enter the cells into useful energy. Pyruvate uptake across the mitochondrial inner membrane is a central branch point in cellular energy metabolism with the ability to balance glycolysis and oxidative phosphorylation and poise catabolic an anabolic metabolism. (See, e.g., Divakaruni et al., *PNAS* 110(14): 5422-5427 (2013)). The mitochondrial pyruvate carrier (MPC) is an inner-membrane transporter that facilitates pyruvate uptake from the cytoplasm to mitochondria. The MPC transports pyruvate into mitochondrial matrix that is required for pyruvate metabolism and is critical for metabolic pathways. (See, e.g., McCommis et al., *Biochem. J.* 466: 443-454 (2015) and McCommis et al., *Cell Metab.* 22(4):682-694 (2015)). It is a central regulator of mitochondrial substrate utilization, and restrictions in mitochondrial pyruvate uptake can potentiate the use of fatty acids and a range of amino acids to fuel cellular energetics and biosynthesis. (See, e.g., Divakaruni et al., *J. Cell Biol.* 216(4): 1091-1105 (2017)).

The MPC contains two proteins, MPC1 and MPC2, that form a carrier complex in the inner mitochondrial membrane. MPC1 and MPC2 have been identified as components of the mitochondrial target of thiazolidinediones (TZDs). See, e.g., Colca et al., *PLOS ONE* 8(5):e61551-e61551 (2013).

Mitochondrial diseases are a group of disorders, each of which involves a mitochondrial dysfunction. Mitochondrial diseases are chronic, genetic, and often inherited disorders that that occur when mitochondria fail to produce enough energy for the body to function properly. Mitochondrial diseases can be present at birth, but can also occur at any age. These diseases can affect the cells of the brain, nerves, muscles, kidneys, heart, liver, eyes, ears, and/or pancreas. Mitochondrial dysfunction occurs when the mitochondria do not work as well as they should due to another disease or condition. Mitochondrial disease refers to a heterogeneous group of disorders that include primary and secondary mitochondrial disorders (See e.g, Niyazov el al., *Mol. Syndromol.* 7:122-137 (2016)). Primary mitochondrial disorders can be due to germline mutations in mitochondrial DNA (mtDNA) and/or nuclear DNA (nDNA) genes either encoding OXPHOS (oxidative phosphorylation) proteins directly or they affect OXPHOS function by impacting production of the complex machinery needed to run the OXPHOS process. Secondary mitochondrial disorders by contrast occur in many pathologic processes not involving OXPHOS, including inherited diseases with germline mutations in non-OXPHOS genes. Secondary mitochondrial disorders can also be acquired secondary to adverse environmental effects which can cause oxidative stress.

Many conditions can lead to secondary mitochondrial disorder including autism, Parkinson's disease, Alzheimer's disease, muscular dystrophy, Lou Gehrig's disease, diabetes and cancer.

Rosiglitazone, a thiazolidinedione, has been reported to bind to the mitochondrial pyruvate carrier (MPC) at physiologic concentrations and acutely suppress pyruvate metabolism (See, e.g., Colca et al., *PLOS ONE* 8(5):e61551-e61551 (2013)). Divakaruni et al. describe that thiazolidinediones are acute, specific inhibitors of MPC, referring to FIG. 3C. See, Divakaruni et al., *PNAS* 110(14):5424 (2013). However, although pioglitazone has been mentioned in the publication, FIG. 3C does not provide any results on MPC inhibition for pioglitazone.

Pioglitazone is a drug marketed for use in the treatment of diabetes mellitus type 2. Pioglitazone is a potent agonist for peroxisome proliferator-activated receptor-gamma (PPAR-γ). But pioglitazone has been associated with unwanted side effects including the potential for drug to drug interactions, cardiovascular effects, fluid retention, weight gain, and bladder cancer (See, e.g., Kus et al., *PLoS ONE* 6(11): e27126 (2011)). High doses and/or chronic administration of pioglitazone are therefore undesirable as high systemic exposure would be likely to result in serious side effects.

Pioglitazone is a "dirty" drug which is converted to many metabolites in vivo. The metabolic pathway of pioglitazone after oral administration has been studied in several animal species and in humans, and the metabolites have been described in the literature (See, e.g., Sohda et al., *Chem. Pharm. Bull.* 43(12):2168-2172 (1995) and Maeshiba et al., *Arzneim.-Forsch/Drug Res.* 47(I):29-35 (1997). At least six metabolites have been identified, named M-I to M-VI. Among these metabolites, M-II, M-III, and M-IV show some pharmacological activity but are less active than pioglitazone in diabetic preclinical models. 5-[[4-[2-[5-(1-hydroxyethyl)pyridin-2-yl]ethoxy]phenyl]methyl]-1,3-thiazolidine-2,4-dione has shown to be effective in the treatment of central nervous system diseases (See WO 2015/150476 A1).

There is an urgent need for new treatments for mitochondrial diseases.

SUMMARY

The present disclosure provides a method of treating or preventing mitochondrial diseases in a patient by administering a compound of formula (1), or a pharmaceutically acceptable salt thereof. In one embodiment, the mitochondrial disease is a primary mitochondrial disorder. In another embodiment, the mitochondrial disease is a secondary mitochondrial disorder.

In another embodiment, the mitochondrial disease is a primary mitochondrial disorder selected from the group consisting of Rett syndrome; Alper's disease; Leber's hereditary optic neuropathy (LHON); Kearns-Sayre syndrome (KSS); Leigh's syndrome; Leigh-like syndrome; maternally inherited Leigh syndrome (MILS); mitochondrial depletion syndrome (MDS); mitochondrial DNA depletion syndrome (MDDS); mitochondrial encephalomyopathy; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; chronic progressive external opthalmoplegia (CPEO); dominant optic atrophy (DOA); autosomal dominant optic atrophy (ADOA); mitochondrial myopathy; cardiomyopathy; mitochondrial encephalopathy; myoclonic epilepsy; maternally inherited diabetes and deafness (MIDD); ataxia neuropathy spectrum; 3-methylglutaconic aciduria; sensoneural deafness; neuroradiological findings of Leigh-like syndrome (MEGDEL); SURF1 (COX deficient Leigh syndrome due to complex IV surfeit protein deficiency); oxidative phosphorylation disorders; Berth syndrome; lethal infantile cardiomyopathy (LIC); pyruvate carboxylase deficiency; pyruvate dehydrogenase deficiency; POLG mutation; isolated or combined OXPHOS deficiencies with so far unsolved genetic defect including disturbed pyruvate oxidation and ATP plus PCr production rates; POLG2 mutation; carnitine-acyl-cartinine deficiency; carnitine deficiency; creatinine deficiency syndromes; Co-Enzyme Q10 deficiency; Complex I deficiency; Complex II deficiency; Complex III deficiency; Complex IV deficiency; Complex V deficiency; lactic acidosis; leukoencephalopathy with brain stem and spinal cord involvement and lactate elevation (LBSL); Luft disease; carnitine palmitoyltransferase (CPT I or CPT II) deficiency; short-chain acyl-CoA dehydrogenase deficiency (SCAD); short-chain 3-hydroxyacetyl-CoA dehydrogenase deficiency (SCHAD); medium-chain acyl-CoA dehydrogenase deficiency (MCAD); multiple acyl-CoA dehydrogenase deficiency (MADD); long-chain acyl-CoA dehydrogenase deficiency (LCAD); very long-chain acyl-CoA dehydrogenase deficiency (VLCAD); trifunctional protein (TFP) deficiency; and glutaric aciduria Type II. In another embodiment, the primary mitochondrial disorder is selected from the group consisting of Rett syndrome; dominant optic atrophy (DOA); autosomal dominant optic atrophy (ADOA); Complex I deficiency; Leber hereditary optic neuropathy (LHON); Kearns-Sayre syndrome (KSS); Leigh's syndrome; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; and chronic progressive external opthalmoplegia (CPEO).

In another embodiment, the mitochondrial disease is a secondary mitochondrial disorder selected from the group consisting of selected from the group consisting of Duchenne muscular dystrophy (DMD); Becker muscular dystrophy (BMD); myotonic dystrophy (BMD); congenital myopathies; glycogen storage disorders; spinal-bulbar muscular atrophy (SBMA); argininosuccinic aciduria; autism spectrum disorder (ASD); autoimmune diseases of the skin (such as pemphigus vulgaris and lupus); methylmalonic and propionic acidurias; disorders or purine and/or pyrimidine synthesis; facioscapulohumeral muscular dystrophy (FSHD); congenital muscular dystrophies; collagen VI muscular dystrophies (e.g., Ullrich congenital muscular dystrophy, Bethlem myopathy, oculopharyngeal distal, and Emery-Dreifuss); DiGeorge syndrome; and neuromuscular disorders (such as limb-girdle muscular dystrophy, inflammatory myopathies, Charcot Marie Tooth (CMT) neuropathy, and drug-induced peripheral neuropathies). In another embodiment, the secondary mitochondrial disorder is Duchenne muscular dystrophy (DMD) or Becker muscular dystrophy (BMD).

The inventors have surprisingly found that compounds of formula (1), and salts thereof, inhibit MPC whereas pioglitazone does not inhibit directly MPC.

The present disclosure provides a method of treating or preventing a mitochondrial disease, wherein the method comprises administering to a subject in need thereof a compound of formula (1)

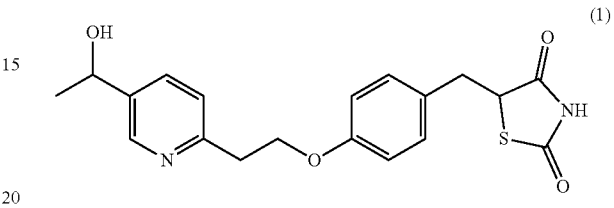

or a pharmaceutically acceptable salt thereof, in an amount effective to treat or prevent a mitochondrial disease. In an embodiment the compound of formula (1) is one or more of compounds: (2) (R)-5-[[4-[2-[5-(R)-(1-hydroxyethyl)pyridin-2-yl]ethoxy]phenyl]methyl]-1,3-thiazolidine-2,4-dione; (3) (R)-5-[[4-[2-[5-(S)-(1-hydroxyethyl)pyridin-2-yl]ethoxy]phenyl]methyl]-1,3-thiazolidine-2,4-dione; (4) (S)-5-[[4-[2-[5-(R)-(1-hydroxyethyl)pyridin-2-yl]ethoxy]phenyl]methyl]-1,3-thiazolidine-2,4-dione; or (5) (S)-5-[[4-[2-[5-(S)-(1-hydroxyethyl)pyridin-2-yl]ethoxy]phenyl]methyl]-1,3-thiazolidine-2,4-dione; or a pharmaceutically acceptable salt thereof. In one embodiment, no more than 1% of the total number of hydrogen atoms per mole of the compound of formula (1) are in the form of the $^2H$ isotope.

In another embodiment, the method of treatment or prevention comprises administering a mixture of two or more of compounds selected from the group consisting of (2), (3), (4), and (5), or a pharmaceutically acceptable salt thereof, wherein the mixture is optically active. In one embodiment, compounds (2) and (3) are administered. In another embodiment, compounds (4) and (5) are administered. In another embodiment, compounds (2) and (4) are administered. In another embodiment, compounds (3) and (5) are administered.

In one aspect of the disclosure, mitochondrial disease is a primary mitochondrial disorder selected from the group consisting of Rett syndrome; Alper's disease; Leber's hereditary optic neuropathy (LHON); Kearns-Sayre syndrome (KSS); Leigh's syndrome; Leigh-like syndrome; maternally inherited Leigh syndrome (MILS); mitochondrial depletion syndrome (MDS); mitochondrial DNA depletion syndrome (MDDS); mitochondrial encephalomyopathy; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; chronic progressive external opthalmoplegia (CPEO); dominant optic atrophy (DOA); autosomal dominant optic atrophy (ADOA); mitochondrial myopathy; cardiomyopathy; mitochondrial encephalopathy; myoclonic epilepsy; maternally inherited diabetes and deafness (MIDD); ataxia neuropathy spectrum; 3-methylglutaconic aciduria; sensoneural deafness; neuroradiological findings of Leigh-like syndrome (MEGDEL); SURF1 (COX deficient Leigh syndrome due to complex IV surfeit protein deficiency); oxidative phosphorylation disorders; Berth syndrome; lethal infantile cardiomyopathy (LIC); pyruvate carboxylase deficiency; pyruvate dehydrogenase deficiency; POLG mutation; isolated or combined OXPHOS deficiencies with so far unsolved genetic defect including disturbed pyruvate oxidation and ATP plus PCr production rates; POLG2 mutation; carnitine-acyl-cartinine deficiency; carnitine deficiency; creatinine deficiency syndromes; Co-Enzyme Q10 deficiency; Complex I deficiency; Complex II deficiency; Complex III deficiency; Complex IV deficiency; Complex V deficiency; lactic acidosis; leukoencephalopathy with brain stem and spinal cord involvement and lactate elevation (LBSL); Luft disease; carnitine palmitoyltransferase (CPT I or CPT II) deficiency; short-chain acyl-CoA dehydrogenase deficiency (SCAD); short-chain 3-hydroxy-acetyl-CoA dehydrogenase deficiency (SCHAD); medium-chain acyl-CoA dehydrogenase deficiency (MCAD); multiple acyl-CoA dehydrogenase deficiency (MADD); long-chain acyl-CoA dehydrogenase deficiency (LCAD); very long-chain acyl-CoA dehydrogenase deficiency (VLCAD); trifunctional protein (TFP) deficiency; and glutaric aciduria Type II.

In another aspect of the disclosure, the mitochondrial disease is a primary mitochondrial disorder selected from the group consisting of Rett syndrome; dominant optic atrophy (DOA); autosomal dominant optic atrophy (ADOA); Complex I deficiency; Leber hereditary optic neuropathy (LHON); Kearns-Sayre syndrome (KSS); Leigh's syndrome; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; and chronic progressive external opthalmoplegia (CPEO).

In another embodiment, the mitochondrial disease is a secondary mitochondrial disorder selected from the group consisting of selected from the group consisting of Duchenne muscular dystrophy (DMD); Becker muscular dystrophy (BMD); myotonic dystrophy (BMD); congenital myopathies; glycogen storage disorders; spinal-bulbar muscular atrophy (SBMA); argininosuccinic aciduria; autism spectrum disorder (ASD); autoimmune diseases of the skin (such as pemphigus vulgaris and lupus); methylmalonic and propionic acidurias; disorders or purine and/or pyrimidine synthesis; facioscapulohumeral muscular dystrophy (FSHD); congenital muscular dystrophies; collagen VI muscular dystrophies (e.g., Ullrich congenital muscular dystrophy, Bethlem myopathy, oculopharyngeal distal, and Emery-Dreifuss); DiGeorge syndrome; and neuromuscular disorders (such as limb-girdle muscular dystrophy, inflammatory myopathies, Charcot Marie Tooth (CMT) neuropathy, and drug-induced peripheral neuropathies).

In another embodiment, the secondary mitochondrial disorder is Duchenne muscular dystrophy (DMD) or Becker muscular dystrophy (BMD).

In another embodiment, the method further comprises administering an additional therapeutic agent. In another embodiment, the compound of formula (1), or a pharmaceutically acceptable salt thereof, is administered to the subject in an oral dosage form, such as a tablet, a capsule, a pill, a plurality of granules, an oral solution or an oral suspension.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

DETAILED DESCRIPTION

Figure 1:
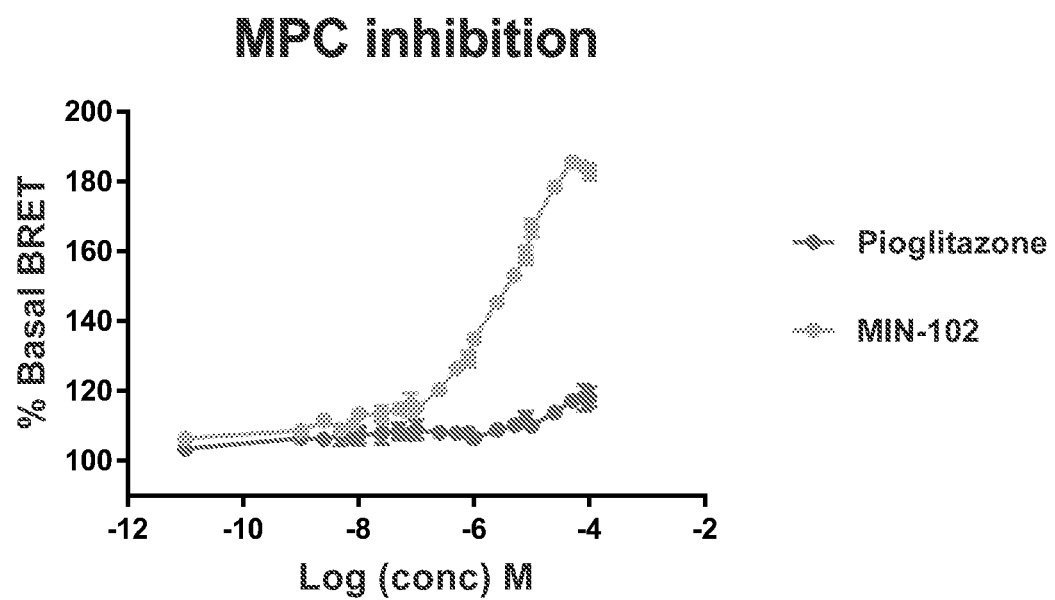
FIG. 1 represents a line graph showing the comparison of the MPC inhibitory effects of 5-[[4-[2-[5-(R)-(1-hydroxyethyl)pyridin-2-yl]ethoxy]phenyl]methyl]-1,3-thiazolidine-2,4-dione HCl (MIN-102) and pioglitazone in an in vitro MPC inhibitory activity model using BRET-assay in HEK cells.

In one aspect, the present disclosure is drawn to a method of treating or preventing a mitochondrial disease, comprising administering to a subject in need thereof an effective amount of a compound of formula (1) or a pharmaceutically acceptable salt thereof, in an amount effective to treat or prevent a mitochondrial disease. In one embodiment, the mitochondrial disease is a primary mitochondrial disorder. In another embodiment, the primary mitochondrial disorder is selected form the group consisting of Rett syndrome; Alper's disease; Leber's hereditary optic neuropathy (LHON); Kearns-Sayre syndrome (KSS); Leigh's syndrome; Leigh-like syndrome; maternally inherited Leigh syndrome (MILS); mitochondrial depletion syndrome (MDS); mitochondrial DNA depletion syndrome (MDDS); mitochondrial encephalomyopathy; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; chronic progressive external opthalmoplegia (CPEO); dominant optic atrophy (DOA); autosomal dominant optic atrophy (ADOA); mitochondrial myopathy; cardiomyopathy; mitochondrial encephalopathy; myoclonic epilepsy; maternally inherited diabetes and deafness (MIDD); ataxia neuropathy spectrum; 3-methylglutaconic aciduria; sensoneural deafness; neuroradiological findings of Leigh-like syndrome (MEGDEL); SURF1 (COX deficient Leigh syndrome due to complex IV surfeit protein deficiency); oxidative phosphorylation disorders; Berth syndrome; lethal infantile cardiomyopathy (LIC); pyruvate carboxylase deficiency; pyruvate dehydrogenase deficiency; POLG mutation; isolated or combined OXPHOS deficiencies with so far unsolved genetic defect including disturbed pyruvate oxidation and ATP plus PCr production rates; POLG2 mutation; carnitine-acyl-cartinine deficiency; carnitine deficiency; creatinine deficiency syndromes; Co-Enzyme Q10 deficiency; Complex I deficiency; Complex II deficiency; Complex III deficiency; Complex IV deficiency; Complex V deficiency; lactic acidosis; leukoencephalopathy with brain stem and spinal cord involvement and lactate elevation (LBSL); Luft disease; carnitine palmitoyltransferase (CPT I or CPT II)

deficiency; short-chain acyl-CoA dehydrogenase deficiency (SCAD); short-chain 3-hydroxyacetyl-CoA dehydrogenase deficiency (SCHAD); medium-chain acyl-CoA dehydrogenase deficiency (MCAD); multiple acyl-CoA dehydrogenase deficiency (MADD); long-chain acyl-CoA dehydrogenase deficiency (LCAD); very long-chain acyl-CoA dehydrogenase deficiency (VLCAD); trifunctional protein (TFP) deficiency; and glutaric aciduria Type II.

In another embodiment, the mitochondrial disease is a primary mitochondrial disorder selected from the group consisting of Rett syndrome; dominant optic atrophy (DOA); autosomal dominant optic atrophy (ADOA); Complex I deficiency; Leber hereditary optic neuropathy (LHON); Kearns-Sayre syndrome (KSS); Leigh's syndrome; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; and chronic progressive external opthalmoplegia (CPEO).

In another embodiment, the mitochondrial disease is a secondary mitochondrial disorder selected from the group consisting of selected from the group consisting of Duchenne muscular dystrophy (DMD); Becker muscular dystrophy (BMD); myotonic dystrophy (BMD); congenital myopathies; glycogen storage disorders; spinal-bulbar muscular atrophy (SBMA); argininosuccinic aciduria; autism spectrum disorder (ASD); autoimmune diseases of the skin (such as pemphigus vulgaris and lupus); methylmalonic and propionic acidurias; disorders or purine and/or pyrimidine synthesis; facioscapulohumeral muscular dystrophy (FSHD); congenital muscular dystrophies; collagen VI muscular dystrophies (e.g., Ullrich congenital muscular dystrophy and Bethlem myopathy); DiGeorge syndrome; and neuromuscular disorders (such as limb-girdle muscular dystrophy, inflammatory myopathies, Charcot Marie Tooth (CMT) neuropathy, and drug-induced peripheral neuropathies). In another embodiment, the collagen muscular dystrophy is oculopharyngeal distal or Emery-Dreifuss.

In another embodiment, the secondary mitochondrial disorder is Duchenne muscular dystrophy (DMD) or Becker muscular dystrophy (BMD).

Also disclosed is a compound of formula (1), or a pharmaceutically acceptable salt thereof, for use in the treatment or prevention of a mitochondrial disease, wherein the mitochondrial diseases are as described above.

Also disclosed is use of a compound of formula (1), or a pharmaceutically acceptable salt thereof, in the manufacture of a medicament for the treatment or prevention of a mitochondrial disease, wherein the mitochondrial diseases are as described above.

It has been unexpectedly discovered that compounds of formula (1)

having the chemical name 5-[[4-[2-[5-(1-hydroxyethyl)pyridin-2-yl]ethoxy]phenyl]methyl]-1,3-thiazolidine-2,4-dione (also called as 5-(4-(2-(5-(1-hydroxyethyl)pyridine-2-yl)ethoxy)benzyl)thiazolidine-2,4-dione, hydroxypioglitazone, hydroxy pioglitazone, or M-IV), and pharmaceutically acceptable salts thereof, collectively referred to herein as "Compounds of the Disclosure" (each is individually referred to hereinafter as a "Compound of the Disclosure") exhibit activity as MPC inhibitors and, thus, are useful in a method of treating or preventing mitochondrial diseases. Compounds of the Disclosure have been found to be inhibitors of MPC having an $IC_{50}$ value of about 4.1 µM in the MPC inhibitory activity test using a BRET-assay in HEK cells as described by Compan et al. in *Molecular Cell* 59:491-501 (2015). To the contrary, the parent compound, pioglitazone was found not to inhibit MPC when tested in the same assay having an $IC_{50}$ value of more than 100 µM. Compounds of the Disclosure have also been found to inhibit oxygen consumption in a MPC dependent manner measured as described by Compan et al., supra.

International Appl. No. PCT/IB2017/057587 discloses that Compounds of the Disclosure possess a lower PK variability than pioglitazone and, therefore, treatment with Compounds of the Disclosure is safer than treatment with pioglitazone. Higher doses of pioglitazone would increase the risk of developing adverse events. International Appl. No. PCT/IB2017/057587 discloses compound of formula (1), and the pharmaceutically acceptable salts thereof, for the treatment of nonalcoholic fatty liver disease ("NAFLD"), nonalcoholic steatohepatitis ("NASH"), and other diseases and disorders.

The compound of formula (1), 5-[[4-[2-[5-(1-hydroxyethyl)pyridin-2-yl]ethoxy]phenyl]methyl]-1,3-thiazolidine-2,4-dione, has two chiral centres. One of them is the carbon atom in the 5-position of the thiazolidine-dione ring and the other asymmetric atom is at position 1 of the hydroxyethyl group as shown by the arrows:

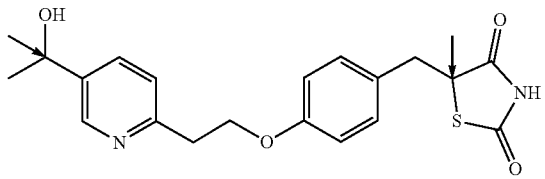

As used herein the term "compound of formula (1)" is used to designate all possible stereoisomers, including enantiomers and diastereomers, and mixtures including racemic mixtures thereof.

In one embodiment, the compound of formula (1) is selected from the group consisting of:

Compound (2): (R)-5-[[4-[2-[5-(R)-(1-hydroxyethyl)pyridin-2-yl]ethoxy]phenyl]methyl]-1,3-thiazolidine-2,4-dione (1)

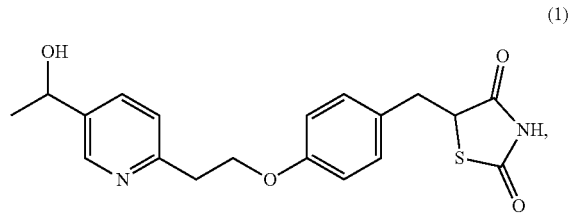 [SMILES: CC(O)c1ccc(CCOc2ccc(CC3SC(=O)NC3=O)cc2)nc1]

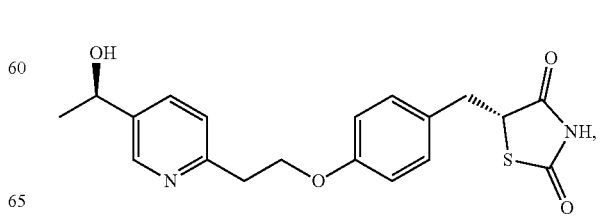

Compound (3): (R)-5-[[4-[2-[5-(S)-(1-hydroxyethyl)pyridin-2-yl]ethoxy]phenyl]methyl]-1,3-thiazolidine-2,4-dione

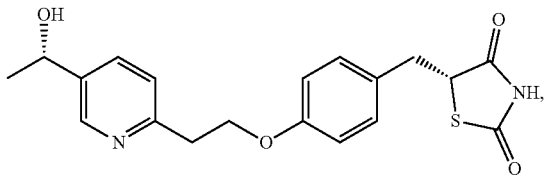 [SMILES: C[C@H](O)c1ccc(CCOc2ccc(C[C@H]3SC(=O)NC3=O)cc2)nc1]

Compound (4): (S)-5-[[4-[2-[5-(R)-(1-hydroxyethyl)pyridin-2-yl]ethoxy]phenyl]methyl]-1,3-thiazolidine-2,4-dione

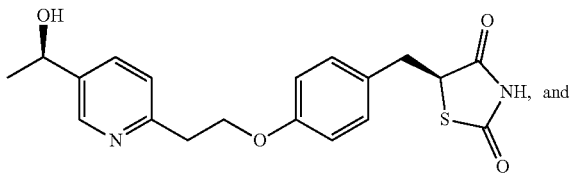 [SMILES: C[C@@H](O)c1ccc(CCOc2ccc(C[C@@H]3SC(=O)NC3=O)cc2)nc1]

and

Compound (5): (S)-5-[[4-[2-[5-(S)-(1-hydroxyethyl)pyridin-2-yl]ethoxy]phenyl]methyl]-1,3-thiazolidine-2,4-dione

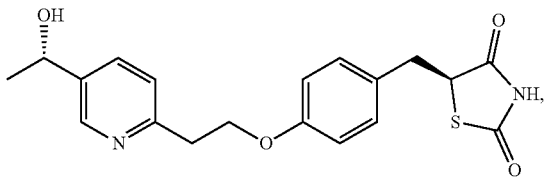 [SMILES: C[C@H](O)c1ccc(CCOc2ccc(C[C@@H]3SC(=O)NC3=O)cc2)nc1]

or a pharmaceutically acceptable salt thereof.

Although compounds (2) to (5) have been prepared as described in WO 2015/150476 A1 and isolated, their absolute (R/S) configuration has not yet been determined. The retention time of each enantiomer has been measured by chiral HPLC.

Reference to compounds (1) to (5) in the present disclosure is intended to designate compounds (1) to (5) having hydrogen atoms which are predominantly in the form of its isotope $^1$H, i.e. no more than 1% of the total number of hydrogen atoms per mole of compound are in the form of the $^2$H isotope (deuterium). In one embodiment, no more than 0.015% (which is the natural abundance of deuterium) of the total number of hydrogen atoms per mole of compound are in the form of the $^2$H isotope (deuterium).

In one embodiment, the patient can be administered a mixture comprising a non-equimolar amount of each compound (2), (3), (4), and (5), or a pharmaceutically acceptable salt thereof. In another embodiment, the mixture comprises each of compound (2), (3), (4), and (5), or a pharmaceutically acceptable salt thereof, in an amount of 20%±10% w/w. In another embodiment, the mixture comprises each of compound (2), (3), (4), and (5), or a pharmaceutically acceptable salt thereof, in an amount of 25%±5% w/w.

In another embodiment, the patient can be administered a mixture comprising each compound (2), (3), (4), and (5), or a pharmaceutically acceptable salt thereof, wherein the mixture comprises an enantiomeric excess of one or more of compound (2), (3), (4), and (5). In another embodiment, the patient can be administered a mixture comprising an equimolar amount of each compound (2), (3), (4), and (5), or a pharmaceutically acceptable salt thereof, i.e., each compound in an amount of 25% w/w.

In one embodiment, the patient can be administered a mixture of two or more compounds selected from the group consisting of compound (2), compound (3), compound (4), and compound (5), or a pharmaceutically acceptable salt thereof, wherein the mixture is optically active. In another embodiment, the mixture comprises two or more compounds selected from the group consisting of:
 (a) the compound (2) and the compound (3);
 (b) the compound (4) and the compound (5);
 (c) the compound (2) and the compound (4); and
 (d) the compound (3) and the compound (5),
or a pharmaceutically acceptable salt thereof.

In another embodiment, the patient is administered the mixture (c) or the mixture (d).

In another embodiment, the patient is administered a mixture consisting essentially of:
 (a) the compound (2) and the compound (3), or a pharmaceutically acceptable salt thereof, as the active agents;
 (b) the compound (4) and the compound (5), or a pharmaceutically acceptable salt thereof, as the active agents;
 (c) the compound (2) and the compound (4), or a pharmaceutically acceptable salt thereof, as the active agents; and
 (d) the compound (3) and the compound (5), or a pharmaceutically acceptable salt thereof, as the active agents.

In another embodiment of the mixtures (a) to (d) mentioned above, the two compounds mentioned in each one of the mixtures are present in equimolar quantities. Said mixtures may comprise also minor amounts (e.g., less than 10 wt. %, less than 3 wt. %, less than 1 wt. %, and less than 0.1 wt. % of another stereoisomer of formula (1)). Said mixtures can also be enantiomerically enriched with respect to one or more compounds (2), (3), (4), and (5).

Another aspect of the disclosure, suitable pharmaceutically acceptable salts of Compounds of the Disclosure include, for example, pharmaceutically acceptable acid addition salts of the Compounds of the Disclosure can be prepared from the following acids, including without limitation, formic, acetic, propionic, benzoic, acetic, propionic, benzoic, succinic, glycolic, gluconic, lactic, maleic, malic, tartaric, citric, nitric, ascorbic, glucuronic, maleic, fumaric, pyruvic, aspartic, glutamic, benzoic, hydrochloric, hydrobromic, hydroiodic, isocitric, xinafoic, tartaric, trifluoroacetic, pamoic, propionic, anthranilic, mesylic, napadisylate, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. In an embodiment, the pharmaceutically acceptable salts include the salts of hydrochloric acid and hydrobromic acid. In an embodiment, the pharmaceutically acceptable salt includes the salt of the hydrochloric acid.

Compounds of the Disclosure can be prepared by any suitable method known in the art, such as by the processes described in WO 2015/150476 A1 and WO 2018/116281 A1. 5-[[4-[2-[5-(1-hydroxyethyl)pyridin-2-yl]ethoxy]phenyl]methyl]-1,3-thiazolidine-2,4-dione is also commercially available from, for example, Santa Cruz Biotechnology and Toronto Research Chemicals (Toronto, Ontario, Canada).

Various examples and embodiments of the inventive subject matter disclosed here are possible and will be apparent to a person of ordinary skill in the art, given the benefit of this disclosure. In this disclosure reference to "some embodiments," "certain embodiments," "certain exemplary embodiments," and similar phrases each means that those embodiments are non-limiting examples of the inventive subject matter, and there are alternative embodiments which are not excluded.

The articles "a," "an," and "the" are used herein to refer to one or to more than one (i.e., to at least one) of the grammatical object of the article. By way of example, "an element" means one element or more than one element.

The word "comprising" is used in a manner consistent with its open-ended meaning, that is, to mean that a given product or process can optionally also have additional features or elements beyond those expressly described. It is understood that wherever embodiments are described with the language "comprising," otherwise analogous embodiments described in terms of "consisting of" and/or "consisting essentially of" are also contemplated and within the scope of this disclosure.

The term "ameliorate" in the context of this present disclosure is understood as meaning any improvement on the situation of the patient treated.

The term "bid administration" or "BID" means twice daily administration of a therapeutic.

The term "SAD" means a single oral dose administration of a therapeutic.

In the present disclosure, each of the terms "compound of formula (1)", "hydroxypioglitazone," "hydroxy pioglitazone (M-IV)," "hydroxy pioglitazone," and "5-[4-[2-(5-(1-hydroxyethyl)-2-pyridinyl)ethoxy]phenyl]-2,4-thiazolidinedione" refer to 5-[[4-[2-[5-(1-hydroxyethyl)pyridin-2-yl]ethoxy]phenyl]methyl]-1,3-thiazolidine-2,4-dione, which has the structure depicted above, and any stereoisomer thereof. The term "MIN-102" refers to the hydrochloride salt of racemic 5-[[4-[2-[5-(1-hydroxyethyl)pyridin-2-yl]ethoxy]phenyl]methyl]-1,3-thiazolidine-2,4-dione.

By an "effective" amount or a "therapeutically effective amount" of a drug or pharmacologically active agent is meant a nontoxic but sufficient amount of the drug or agent to provide the desired effect. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The term "treatment" or "to treat" in the context of this specification means to ameliorate or eliminate the disease or one or more symptoms associated with said disease. "Treatment" also encompasses ameliorating or eliminating the physiological sequelae of the disease.

As used herein, the phrase "PK variability" or "pharmacokinetic variability" refer to inter-individual variations of a drugs pharmacokinetic parameters, resulting in different plasma concentration-time profiles after administration of the same dose to different patients.

The term "pharmaceutically acceptable salt" refers to salts prepared from pharmaceutically acceptable inorganic and organic acids.

The term "prevention" or "to prevent" refers to the reduction in the risk of acquiring or developing a given disease or disorder, or the reduction or inhibition of the recurrence or a disease or disorder.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as $|R-S|*100$, where R and S are the respective mole or weight fractions of enantiomers in a mixture such that $R+S=1$. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

The term "primary mitochondrial disorder" or "PMD" refers to a mitochondrial disease that can occur due to germline mutations in mitochondrial DNA (mtDNA) and/or nuclear DNA (nDNA) genes encoding the electron transport chain (ETC) proteins and therefore the production of adenosine-triphosphate (ATP), the major cellular energy carrier.

The term "secondary mitochondrial disorder" or "SMD" refers to a mitochondrial disease accompanying many pathologic processes not involving oxidative phosphorylation (OXPHOS), including inherited diseases with germline mutations in non-OXPHOS genes. SMD can also be acquired secondary to adverse environmental effects which can cause oxidative stress.

Methods of Treatment or Prevention

The utility of the compound of formula (1) in the present method, including stereoisomers (2) to (5), mixtures (a) to (d), and pharmaceutically acceptable salts thereof can be demonstrated in appropriate in vitro or in vivo assays, such as, as described, for example, in Compan et al., *Molecular Cell* 59:491-501 (2015); Abou-Samra et al., *Skeletal Muscle* 5:25 (2015); (McGreevy et al., *Disease Models & Mechanisms* 8:195-213 (2015); Bostick et al., *Circulation Research Han.* 4/18:121-130 (2008); Bostick et al., *Molecular Therapy* 17(2):253-261 (2009); Zanou et al., *J. Physiol.* 593.17:3849-3863 (2010); and Signorini et al., *Oxidative Medicine and Cellular Longevity* Volume 2014, Article ID 195935, 10 pages (2014).

As shown in Example 1, the MPC inhibitory potential of MIN-102 was studied using BRET-assay in HEK cells according to Compan et al., *Molecular Cell* 59:491-501 (2015). The dose response curve of FIG. 1 shows that MIN-102 has an $IC_{50}$ value of 4.1 µM in the BRET-assay, whereas pioglitazone has an $IC_{50}$ value of more than 100 µM. Accordingly, MIN-102 displays an MPC inhibitory effect and pioglitazone does not inhibit MPC. Based on their MPC inhibitory activity, Compounds of the Disclosure can be useful in treating or preventing of mitochondrial diseases. See, e.g., Divakaruni et al., *PNAS* 110(14):5422-5427 (2013).

In addition, Compounds of the Disclosure have activity as PPAR-γ agonists. See, e.g., WO 2015/150476 A1. The combined activity of Compounds of the Invention as MPC inhibitors and PPAR-γ agonists is expected to make Compounds of the Disclosure especially useful in the treatment and/or prevention of mitochondrial diseases described herein.

Example 1 also shows that MIN-102 inhibits oxygen consumption in a MPC dependent manner.

Furthermore, as discussed in International Appl. No. PCT/IB2017/057587, in humans MIN-102 has less variability in exposure than pioglitazone and, therefore, less risks for the patients are involved with treatment with Compounds of the Disclosure, such as MIN-102.

Pharmaceutical Compositions and Use as a Medicament

Pharmaceutical compositions comprising a Compound of the Disclosure can be administered by any suitable route of administration. For example, any of oral, intraoral, topical, epicutaneous, subcutaneous, transdermal, intramuscular, parenteral, ocular, rectal, vaginal, inhalation, buccal, sublingual and intranasal delivery routes can be suitable. The present disclosure also relates to the use of a compound of formula (1), or a pharmaceutically acceptable salt thereof, in the manufacture of a medicament for the treatment or prevention of a mitochondrial disease. In one embodiment, the mitochondrial disease is a primary mitochondrial disorder selected from the group consisting of Rett syndrome; Alper's disease; Leber's hereditary optic neuropathy (LHON); Kearns-Sayre syndrome (KSS); Leigh's syndrome; Leigh-like syndrome; maternally inherited Leigh syndrome (MILS); mitochondrial depletion syndrome (MDS); mitochondrial DNA depletion syndrome (MDDS); mitochondrial encephalomyopathy; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; chronic progressive external opthalmoplegia (CPEO); dominant optic atrophy (DOA); autosomal dominant optic atrophy (ADOA); mitochondrial myopathy; cardiomyopathy; mitochondrial encephalopathy; myoclonic epilepsy; maternally inherited diabetes and deafness (MIDD); ataxia neuropathy spectrum; 3-methylglutaconic aciduria; sensoneural deafness; neuroradiological findings of Leigh-like syndrome (MEGDEL); SURF1 (COX deficient Leigh syndrome due to complex IV surfeit protein deficiency); oxidative phosphorylation disorders; Berth syndrome; lethal infantile cardiomyopathy (LIC); pyruvate carboxylase deficiency; pyruvate dehydrogenase deficiency; POLG mutation; isolated or combined OXPHOS deficiencies with so far unsolved genetic defect including disturbed pyruvate oxidation and ATP plus PCr production rates; POLG2 mutation; carnitine-acyl-cartinine deficiency; carnitine deficiency; creatinine deficiency syndromes; Co-Enzyme Q10 deficiency; Complex I deficiency; Complex II deficiency; Complex III deficiency; Complex IV deficiency; Complex V deficiency; lactic acidosis; leukoencephalopathy with brain stem and spinal cord involvement and lactate elevation (LBSL); Luft disease; carnitine palmitoyltransferase (CPT I or CPT II) deficiency; short-chain acyl-CoA dehydrogenase deficiency (SCAD); short-chain 3-hydroxyacetyl-CoA dehydrogenase deficiency (SCHAD); medium-chain acyl-CoA dehydrogenase deficiency (MCAD); multiple acyl-CoA dehydrogenase deficiency (MADD); long-chain acyl-CoA dehydrogenase deficiency (LCAD); very long-chain acyl-CoA dehydrogenase deficiency (VLCAD); trifunctional protein (TFP) deficiency; and glutaric aciduria Type II.

In another embodiment, the mitochondrial disease is a primary mitochondrial disorder selected from the group consisting of Rett syndrome; dominant optic atrophy (DOA); autosomal dominant optic atrophy (ADOA); Complex I deficiency; Leber hereditary optic neuropathy (LHON); Kearns-Sayre syndrome (KSS); Leigh's syndrome; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; and chronic progressive external opthalmoplegia (CPEO).

In another embodiment, the mitochondrial disease is a secondary mitochondrial disorder selected from the group consisting of selected from the group consisting of Duchenne muscular dystrophy (DMD); Becker muscular dystrophy (BMD); myotonic dystrophy (BMD); congenital myopathies; glycogen storage disorders; spinal-bulbar muscular atrophy (SBMA); argininosuccinic aciduria; autism spectrum disorder (ASD); autoimmune diseases of the skin (such as pemphigus vulgaris and lupus); methylmalonic and propionic acidurias; disorders or purine and/or pyrimidine synthesis; facioscapulohumeral muscular dystrophy (FSHD); congenital muscular dystrophies; collagen VI muscular dystrophies (e.g., Ullrich congenital muscular dystrophy, Bethlem myopathy, oculopharyngeal distal, and Emery-Dreifuss); DiGeorge syndrome; and neuromuscular disorders (such as limb-girdle muscular dystrophy, inflammatory myopathies, Charcot Marie Tooth (CMT) neuropathy, and drug-induced peripheral neuropathies).

In another embodiment, the secondary mitochondrial disorder is Duchenne muscular dystrophy (DMD) or Becker muscular dystrophy (BMD).

In one embodiment, Compounds of the Disclosure can be administered orally. Oral forms of pharmaceutical compositions can be solid or liquid. Suitable oral dosage forms include tablets, capsules, pills, granules, suspensions, emulsions, syrups or solutions. The pharmaceutical compositions may be a solid form selected from, e.g., tablets, capsules, pills, or granules. In an embodiment, the oral form is a tablet. In another embodiment, the oral form is an oral solution or suspension. These are advantageous when the patient has difficulty swallowing, for example as a result of the disease or for geriatric and pediatric use. Sublingual preparations are also advantageous.

The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation. Thus, the dose of the active agent will depend on the nature and degree of the condition, the age and condition of the patient, and other factors known to those skilled in the art. A typical daily dosage is from 0.1 to 200 mg, such as from 20 to 200 mg, e.g., for an adult 10-100 mg given as a single dose with no further dosing or in multiple doses, for example one to three times per day. Compounds of the Description described herein may also be administered in daily doses for adults of from 80 to 600 mg. In one embodiment the daily dose for adults is from about 50 mg to about 300 mg. In another embodiment the daily dose for adults is from about 150 mg to about 180 mg. Lower daily doses for children and teens can be used, such as for example, 0.1 mg to 200 mg or from 10 mg to 100 mg.

The pharmaceutical compositions may contain conventional excipients known in the art and may be prepared by conventional methods. A specific compound or mixture of compounds may be selected for a particular route of delivery. Some compounds or mixtures of compounds may also be suitable based on their use to treat mitochondrial diseases.

Oral dosage forms may be prepared by combining one or more Compounds of the Disclosure in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, stabilizers, and disintegrating agents.

Due to their ease of administration, tablets, caplets, and capsules (such as hard gelatin, HPMC, or starch capsules) represent an embodiment of the solid oral dosage unit forms, in which case solid pharmaceutical excipients are used. If desired, tablets or caplets can be coated by standard aqueous or nonaqueous techniques. These dosage forms can be prepared by any of the methods of pharmacy. In general, pharmaceutical compositions and dosage forms are prepared by uniformly and intimately admixing one or more Compounds of the Disclosure with liquid carriers, finely divided solid carriers, or both, and then shaping the product into the desired presentation if necessary.

For example, a tablet can be prepared by compression or molding. Compressed tablets can be prepared by compressing in a suitable machine one or more Compounds of the Disclosure in a free-flowing form, such as a powder or granules, optionally mixed with one or more excipients. Molded tablets can be made by molding in a suitable machine a mixture of the powdered compound moistened with an inert liquid diluent.

The pharmaceutical compositions may further comprise one or more other therapeutic agents. Combination treatments may be administered simultaneously, sequentially, or separately, by the same or by different routes, or before, during, and after surgical or intervention procedures.

Compounds of the Disclosure can be used according to the disclosure when the patient is also administered or in combination with one or more of another therapeutic agent selected from antiinflammatory and analgesic agents, antidiabetics (e.g., metformin), dopamine agonists (e.g. levodopa), MAO-B inhibitors, catechol O-methyltransferase (COMT) inhibitors, anticholinergics, other antiparkinsonians (e.g. amantadine), antiNMDA receptors (e.g. memantine), cholinesterase inhibitors, ACE inhibitors, glutamate antagonist (e.g. riluzole), antioxidants, immunomodulators (e.g. fingolimod, anti CD52, CD25 and CD20 monoclonal antibodies, interferon-β-1a, natalizumab, laquinimod, dimethylfumarate) chemotherapeutics, enzyme replacement therapy agents, substrate reduction therapy agents, corticosteroids, antiproliferatives (e.g. methotrexate), anticonvulsant medications, anticoagulants, antihypertensives and neuroprotectives. The compounds of the disclosure may also be used when the patient is undergoing gene therapy, bone marrow transplantation, deep brain stimulation or radiotherapy.

The one or more therapeutic agents include a sulfonylurea (e.g., glimepiride, glipizide, glyburide), a glinidine (also known as meglitinides), a thiazolidinedione (e.g., pioglitazone, rosiglitazone, lobeglitazone), a dipeptidyl peptidase 4 (DPP4) inhibitor (e.g., sitagliptin, vildagliptin, saxagliptin, linagliptin, gemigliptin, anagliptin, teneligliptin, alogliptin, trelagliptin, dutogliptin, omarigliptin), a sodium/glucose cotransporter 2 (SGLT2) inhibitor (e.g., canagliflozin, dapagliflozin), a glucagon-like peptide-1 (GLP1) receptor agonist (e.g., exenatide, liraglutide, lixisenatide, albiglutide, dulaglutide, taspoglutide, semaglutide), glucagon like peptide-1 (GLP-1), and insulin (e.g., animal insulin preparations extracted from the pancreas of cattle or pigs; human insulin preparations synthesized by genetic engineering using *Escherichia coli* or yeast; insulin zinc; protamine insulin zinc; insulin fragments or derivatives (e.g., INS-1), and oral insulin preparations.

Particular Embodiments of the Disclosure

The disclosure also provides the following particular embodiments relating to the uses and methods of treating a disease or disorder in a patient in need thereof.

Embodiment 1. A compound of formula (1), or a pharmaceutically acceptable salt thereof, for use in the treatment or prevention of a mitochondrial disease

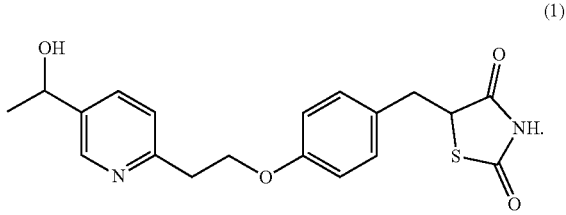 [SMILES: CC(O)c1ccc(CCOc2ccc(CC3SC(=O)NC3=O)cc2)nc1]

(1)

Embodiment 2. The compound for use of Embodiment 1, wherein the mitochondrial disease is a primary mitochondrial disorder selected from the group consisting of Rett syndrome, Alper's disease; Leber's hereditary optic neuropathy (LHON); Kearns-Sayre syndrome (KSS); Leigh's syndrome; Leigh-like syndrome; maternally inherited Leigh syndrome (MILS); mitochondrial depletion syndrome (MDS); mitochondrial DNA depletion syndrome (MDDS); mitochondrial encephalomyopathy; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; chronic progressive external opthalmoplegia (CPEO); dominant optic atrophy (DOA); autosomal dominant optic atrophy (ADOA); mitochondrial myopathy; cardiomyopathy; mitochondrial encephalopathy; myoclonic epilepsy; maternally inherited diabetes and deafness (MIDD); ataxia neuropathy spectrum; 3-methylglutaconic aciduria; sensoneural deafness; neuroradiological findings of Leigh-like syndrome (MEGDEL); SURF1 (COX deficient Leigh syndrome due to complex IV surfeit protein deficiency); oxidative phosphorylation disorders; Berth syndrome; lethal infantile cardiomyopathy (LIC); pyruvate carboxylase deficiency; pyruvate dehydrogenase deficiency; POLG mutation; isolated or combined OXPHOS deficiencies with so far unsolved genetic defect including disturbed pyruvate oxidation and ATP plus PCr production rates; POLG2 mutation; carnitine-acyl-cartinine deficiency; carnitine deficiency; creatinine deficiency syndromes; Co-Enzyme Q10 deficiency; Complex I deficiency; Complex II deficiency; Complex III deficiency; Complex IV deficiency; Complex V deficiency; lactic acidosis; leukoencephalopathy with brain stem and spinal cord involvement and lactate elevation (LBSL); Luft disease; carnitine palmitoyltransferase (CPT I or CPT II) deficiency; short-chain acyl-CoA dehydrogenase deficiency (SCAD); short-chain 3-hydroxyacetyl-CoA dehydrogenase deficiency (SCHAD); medium-chain acyl-CoA dehydrogenase deficiency (MCAD); multiple acyl-CoA dehydrogenase deficiency (MADD); long-chain acyl-CoA dehydrogenase deficiency (LCAD); very long-chain acyl-CoA dehydrogenase deficiency (VLCAD); trifunctional protein (TFP) deficiency; and glutaric aciduria Type II.

Embodiment 3. The compound for use of Embodiment 2, wherein the mitochondrial disease is selected from the group consisting of Rett syndrome; dominant optic atrophy (DOA); autosomal dominant optic atrophy (ADOA); Complex I deficiency; Leber hereditary optic neuropathy (LHON); Kearns-Sayre syndrome (KSS); Leigh's syndrome; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; and chronic progressive external opthalmoplegia (CPEO).

Embodiment 4. The compound for use of Embodiment 1, wherein the mitochondrial disease is a secondary mitochondrial disorder selected from the group consisting of Duchenne muscular dystrophy (DMD); Becker muscular dystrophy (BMD); myotonic dystrophy (BMD); congenital myopathies; glycogen storage disorders; spinal-bulbar muscular atrophy (SBMA); argininosuccinic aciduria; autism spectrum disorder (ASD); autoimmune diseases of the skin (such as pemphigus vulgaris and lupus); methylmalonic and propionic acidurias; disorders or purine and/or pyrimidine synthesis; facioscapulohumeral muscular dystrophy (FSHD); congenital muscular dystrophies; collagen VI muscular dystrophies (e.g., Ullrich congenital muscular dystrophy and Bethlem myopathy); DiGeorge syndrome; and neuromuscular disorders (such as limb-girdle muscular dystrophy, inflammatory myopathies, Charcot Marie Tooth (CMT) neuropathy, and drug-induced peripheral neuropathies).

Embodiment 5. The compound for use of Embodiment 4, wherein the mitochondrial disease is Duchenne muscular dystrophy (DMD) or Becker muscular dystrophy (BMD).

Embodiment 6. The compound for use of any one of Embodiments 1-5, wherein the compound of formula (1) is:
compound (2): (R)-5-[[4-[2-[5-(R)-(1-hydroxyethyl)pyridin-2-yl]ethoxy]-phenyl]methyl]-1,3-thiazolidine-2,4-dione;
compound (3): (R)-5-[[4-[2-[5-(S)-(1-hydroxyethyl)pyridin-2-yl]ethoxy]-phenyl]methyl]-1,3-thiazolidine-2,4-dione;
compound (4): (S)-5-[[4-[2-[5-(R)-(1-hydroxyethyl)pyridin-2-yl]ethoxy]-phenyl]methyl]-1,3-thiazolidine-2,4-dione;
or
compound (5): (S)-5-[[4-[2-[5-(S)-(1-hydroxyethyl)pyridin-2-yl]ethoxy]-phenyl]methyl]-1,3-thiazolidine-2,4-dione;
or a pharmaceutically acceptable salt thereof.

Embodiment 7. The compound for use of any one of Embodiments 1-6, wherein no more than 1% of the total number of hydrogen atoms per mole of the compound of formula (1) are in the form of the $^2$H isotope.

Embodiment 8. A mixture of two or more of compounds selected from the group consisting of compound (2), compound (3), compound (4), and compound (5) as defined in Embodiment 6, or a pharmaceutically acceptable salt thereof, for use in the treatment or prevention of a mitochondrial disease or dysfunction.

Embodiment 9. The mixture for use of Embodiment 8, wherein said mixture comprises:
(a) the compound (2) and the compound (3);
(b) the compound (4) and the compound (5);
(c) the compound (2) and the compound (4); or
(d) the compound (3) and the compound (5),
or a pharmaceutically acceptable salt thereof.

Embodiment 10. A mixture of a compound (2), compound (3), compound (4), and compound (5) of Embodiment 8, or a pharmaceutically acceptable salt thereof, for use in the treatment or prevention of a mitochondrial disease or dysfunction, wherein the mixture comprises each compound in an amount of 25%±5% w/w.

Embodiment 11. A method of treating or preventing a mitochondrial disease, comprising administering to a subject in need thereof a compound of formula (1)

(1)

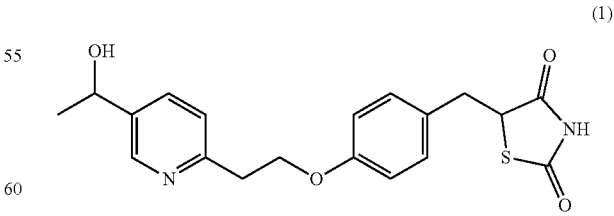

or a pharmaceutically acceptable salt thereof, in an amount effective to treat or prevent said mitochondrial disease.

Embodiment 12. The method of Embodiment 11, wherein the mitochondrial disease is selected from the group consisting of wherein the mitochondrial disease is a primary mitochondrial disorder selected from the group consisting of Rett syndrome, Alper's disease; Leber's hereditary optic neuropathy (LHON); Kearns-Sayre syndrome (KSS); Leigh's syndrome; Leigh-like syndrome; maternally inherited Leigh syndrome (MILS); mitochondrial depletion syndrome (MDS); mitochondrial DNA depletion syndrome (MDDS); mitochondrial encephalomyopathy; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; chronic progressive external opthalmoplegia (CPEO); dominant optic atrophy (DOA); autosomal dominant optic atrophy (ADOA); mitochondrial myopathy; cardiomyopathy; mitochondrial encephalopathy; myoclonic epilepsy; maternally inherited diabetes and deafness (MIDD); ataxia neuropathy spectrum; 3-methylglutaconic aciduria; sensoneural deafness; neuroradiological findings of Leigh-like syndrome (MEGDEL); SURF1 (COX deficient Leigh syndrome due to complex IV surfeit protein deficiency); oxidative phosphorylation disorders; Berth syndrome; lethal infantile cardiomyopathy (LIC); pyruvate carboxylase deficiency; pyruvate dehydrogenase deficiency; POLG mutation; isolated or combined OXPHOS deficiencies with so far unsolved genetic defect including disturbed pyruvate oxidation and ATP plus PCr production rates; POLG2 mutation; carnitine-acyl-cartinine deficiency; carnitine deficiency; creatinine deficiency syndromes; Co-Enzyme Q10 deficiency; Complex I deficiency; Complex II deficiency; Complex III deficiency; Complex IV deficiency; Complex V deficiency; lactic acidosis; leukoencephalopathy with brain stem and spinal cord involvement and lactate elevation (LBSL); Luft disease; carnitine palmitoyltransferase (CPT I or CPT II) deficiency; short-chain acyl-CoA dehydrogenase deficiency (SCAD); short-chain 3-hydroxyacetyl-CoA dehydrogenase deficiency (SCHAD); medium-chain acyl-CoA dehydrogenase deficiency (MCAD); multiple acyl-CoA dehydrogenase deficiency (MADD); long-chain acyl-CoA dehydrogenase deficiency (LCAD); very long-chain acyl-CoA dehydrogenase deficiency (VLCAD); trifunctional protein (TFP) deficiency; and glutaric aciduria Type II.

Embodiment 13. The method of Embodiment 12, wherein the mitochondrial disease is selected from the group consisting of Rett syndrome; dominant optic atrophy (DOA); autosomal dominant optic atrophy (ADOA); Complex I deficiency; Leber hereditary optic neuropathy (LHON); Kearns-Sayre syndrome (KSS); Leigh's syndrome; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; and chronic progressive external opthalmoplegia (CPEO).

Embodiment 14. The method of Embodiment 11, wherein the mitochondrial disease is a secondary mitochondrial disorder selected from the group consisting of Duchenne muscular dystrophy (DMD); Becker muscular dystrophy (BMD); myotonic dystrophy (BMD); congenital myopathies; glycogen storage disorders; spinal-bulbar muscular atrophy (SBMA); argininosuccinic aciduria; autism spectrum disorder (ASD); autoimmune diseases of the skin (such as pemphigus vulgaris and lupus); methylmalonic and propionic acidurias; disorders or purine and/or pyrimidine synthesis; facioscapulohumeral muscular dystrophy (FSHD); congenital muscular dystrophies; collagen VI muscular dystrophies (e.g., Ullrich congenital muscular dystrophy and Bethlem myopathy); DiGeorge syndrome; and neuromuscular disorders (such as limb-girdle muscular dystrophy, inflammatory myopathies, Charcot Marie Tooth (CMT) neuropathy, and drug-induced peripheral neuropathies).

Embodiment 15. The method of Embodiment 14, wherein the mitochondrial disease is Duchenne muscular dystrophy (DMD) or Becker muscular dystrophy (BMD).

Embodiment 16. The method of any one of Embodiments 11 to 15, wherein the compound of formula (1) is selected from the group consisting of:

compound (2): (R)-5-[[4-[2-[5-(R)-(1-hydroxyethyl)pyridin-2-yl]ethoxy]-phenyl]methyl]-1,3-thiazolidine-2,4-dione;

compound (3): (R)-5-[[4-[2-[5-(S)-(1-hydroxyethyl)pyridin-2-yl]ethoxy]-phenyl]methyl]-1,3-thiazolidine-2,4-dione;

compound (4): (S)-5-[[4-[2-[5-(R)-(1-hydroxyethyl)pyridin-2-yl]ethoxy]-phenyl]methyl]-1,3-thiazolidine-2,4-dione; and compound (5): (S)-5-[[4-[2-[5-(S)-(1-hydroxyethyl)pyridin-2-yl]ethoxy]-phenyl]methyl]-1,3-thiazolidine-2,4-dione;

or a pharmaceutically acceptable salt thereof.

Embodiment 17. The method of Embodiment 16, comprising administering a mixture of two or more of compounds selected from the group consisting of compound (2), compound (3), compound (4), and compound (5), or a pharmaceutically acceptable salt thereof.

Embodiment 18. The method of Embodiment 17, wherein the mixture comprises:
  (a) the compound (2) and the compound (3);
  (b) the compound (4) and the compound (5);
  (c) the compound (2) and the compound (4); or
  (d) the compound (3) and the compound (5),
or a pharmaceutically acceptable salt thereof.

Embodiment 19. The method of Embodiment 17, comprising administering a mixture comprising each compound (2), compound (3), compound (4), and compound (5) in an amount of 25%±5% w/w.

Embodiment 20. The method of any one of Embodiments 11 to 19, further comprising administering another therapeutic agent.

Embodiment 21. The method of Embodiment 20, wherein the compound of formula (1), or a pharmaceutically acceptable salt thereof, and said another therapeutic agent are provided in combination.

Embodiment 22. The method of one of Embodiments 11 to 21, wherein no more than 1% of the total number of hydrogen atoms per mole of the compound of formula (1) are in the form of the $^{2}H$ isotope.

Embodiment 23. The method of any one of Embodiments 11 to 22, wherein the compound of formula (1), or a pharmaceutically acceptable salt thereof, is administered to the subject in an oral, intraoral, topical, epicutaneous, subcutaneous, transdermal, intramuscular, parenteral, ocular, rectal, vaginal, inhalation, buccal, sublingual, or intranasal dosage form.

Embodiment 24. The method of Embodiment 23, wherein the dosage form is an oral dosage form.

Embodiment 25. The method of Embodiment 24, wherein the oral dosage form is solid.

Embodiment 26. The method of Embodiment 25, wherein the oral solid dosage form is a tablet, a capsule, a pill, or a plurality of granules.

Embodiment 27. The method of Embodiment 24, wherein the oral dosage form is an oral solution or an oral suspension.

Embodiment 28. Use of a compound of formula (1), or a pharmaceutically acceptable salt thereof, in the manufacture of a medicament for the treatment or prevention of a mitochondrial disease

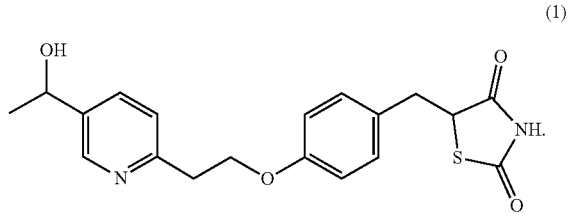 [SMILES: CC(O)c1ccc(CCOc2ccc(CC3SC(=O)NC3=O)cc2)nc1]

(1)

Embodiment 29. The use of Embodiment 28, wherein the mitochondrial disease is a primary mitochondrial disorder selected from the group consisting of Rett syndrome, Alper's disease; Leber's hereditary optic neuropathy (LHON); Kearns-Sayre syndrome (KSS); Leigh's syndrome; Leigh-like syndrome; maternally inherited Leigh syndrome (MILS); mitochondrial depletion syndrome (MDS); mitochondrial DNA depletion syndrome (MDDS); mitochondrial encephalomyopathy; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; chronic progressive external opthalmoplegia (CPEO); dominant optic atrophy (DOA); autosomal dominant optic atrophy (ADOA); mitochondrial myopathy; cardiomyopathy; mitochondrial encephalopathy; myoclonic epilepsy; maternally inherited diabetes and deafness (MIDD); ataxia neuropathy spectrum; 3-methylglutaconic aciduria; sensoneural deafness; neuroradiological findings of Leigh-like syndrome (MEGDEL); SURF1 (COX deficient Leigh syndrome due to complex IV surfeit protein deficiency); oxidative phosphorylation disorders; Berth syndrome; lethal infantile cardiomyopathy (LIC); pyruvate carboxylase deficiency; pyruvate dehydrogenase deficiency; POLG mutation; isolated or combined OXPHOS deficiencies with so far unsolved genetic defect including disturbed pyruvate oxidation and ATP plus PCr production rates; POLG2 mutation; carnitine-acyl-cartinine deficiency; carnitine deficiency; creatinine deficiency syndromes; Co-Enzyme Q10 deficiency; Complex I deficiency; Complex II deficiency; Complex III deficiency; Complex IV deficiency; Complex V deficiency; lactic acidosis; leukoencephalopathy with brain stem and spinal cord involvement and lactate elevation (LBSL); Luft disease; carnitine palmitoyltransferase (CPT I or CPT II) deficiency; short-chain acyl-CoA dehydrogenase deficiency (SCAD); short-chain 3-hydroxyacetyl-CoA dehydrogenase deficiency (SCHAD); medium-chain acyl-CoA dehydrogenase deficiency (MCAD); multiple acyl-CoA dehydrogenase deficiency (MADD); long-chain acyl-CoA dehydrogenase deficiency (LCAD); very long-chain acyl-CoA dehydrogenase deficiency (VLCAD); trifunctional protein (TFP) deficiency; and glutaric aciduria Type II.

Embodiment 30. The use of Embodiment 29, wherein the mitochondrial disease is selected from the group consisting of Rett syndrome; dominant optic atrophy (DOA); autosomal dominant optic atrophy (ADOA); Complex I deficiency; Leber hereditary optic neuropathy (LHON); Kearns-Sayre syndrome (KSS); Leigh's syndrome; mitochondrial encephalomyopathy with lactic acidosis and stroke-like episodes (MELAS); myoclonic epilepsy with ragged red fibers (MERRF); mitochondrial neurogastrointestinal encephalopathy syndrome (MNGIE); neuropathy, ataxia, and retinitis pigmentosa (NARP); Pearson syndrome; and chronic progressive external opthalmoplegia (CPEO).

Embodiment 31. The use of Embodiment 28, wherein the mitochondrial disease is a secondary mitochondrial disorder selected from the group consisting of Duchenne muscular dystrophy (DMD); Becker muscular dystrophy (BMD); myotonic dystrophy (BMD); congenital myopathies; glycogen storage disorders; spinal-bulbar muscular atrophy (SBMA); argininosuccinic aciduria; autism spectrum disorder (ASD); autoimmune diseases of the skin (such as pemphigus vulgaris and lupus); methylmalonic and propionic acidurias; disorders or purine and/or pyrimidine synthesis; facioscapulohumeral muscular dystrophy (FSHD); congenital muscular dystrophies; collagen VI muscular dystrophies (e.g., Ullrich congenital muscular dystrophy and Bethlem myopathy); DiGeorge syndrome; and neuromuscular disorders (such as limb-girdle muscular dystrophy, inflammatory myopathies, Charcot Marie Tooth (CMT) neuropathy, and drug-induced peripheral neuropathies).

Embodiment 32. The use of Embodiment 31, wherein the mitochondrial disease is Duchenne muscular dystrophy (DMD) or Becker muscular dystrophy (BMD).

Embodiment 33. The use of any one of Embodiments 28-32, wherein the compound of formula (1) is:
compound (2): (R)-5-[[4-[2-[5-(R)-(1-hydroxyethyl)pyridin-2-yl]ethoxy]-phenyl]methyl]-1,3-thiazolidine-2,4-dione;
compound (3): (R)-5-[[4-[2-[5-(S)-(1-hydroxyethyl)pyridin-2-yl]ethoxy]-phenyl]methyl]-1,3-thiazolidine-2,4-dione;
compound (4): (S)-5-[[4-[2-[5-(R)-(1-hydroxyethyl)pyridin-2-yl]ethoxy]-phenyl]methyl]-1,3-thiazolidine-2,4-dione; or
compound (5): (S)-5-[[4-[2-[5-(S)-(1-hydroxyethyl)pyridin-2-yl]ethoxy]-phenyl]methyl]-1,3-thiazolidine-2,4-dione;
or a pharmaceutically acceptable salt thereof.

Embodiment 34. The use of any one of Embodiments 28 to 33, wherein no more than 1% of the total number of hydrogen atoms per mole of the compound of formula (1) are in the form of the $^{2}H$ isotope.

Embodiment 35. The use of Embodiment 33 or 34, wherein said medicament comprises a mixture of two or more of compounds selected from the group consisting of compound (2), compound (3), compound (4), and compound (5), or a pharmaceutically acceptable salt thereof.

Embodiment 36. The use of Embodiment 35, wherein the mixture is optically active.

Embodiment 37. The use of Embodiment 35 or 36, wherein said mixture comprises:
(a) the compound (2) and the compound (3);
(b) the compound (4) and the compound (5);
(c) the compound (2) and the compound (4); or
(d) the compound (3) and the compound (5),
or a pharmaceutically acceptable salt thereof.

Embodiment 38. The use of Embodiments 35 or 36, wherein said medicament comprises a mixture of each compound (2), compound (3), compound (4), and compound (5), or a pharmaceutically acceptable salt thereof, in an amount of 25%±5% w/w.

Embodiment 39. The use of any one of Embodiments 28 to 38, wherein said medicament is formulated in an oral, intraoral, topical, epicutaneous, subcutaneous, transdermal, intramuscular, parenteral, ocular, rectal, vaginal, inhalation, buccal, sublingual, or intranasal dosage form.

Embodiment 40. The use of Embodiment 39, wherein the dosage form is an oral dosage form.

Embodiment 41. The use of Embodiment 40, wherein the oral dosage form is solid.

Embodiment 42. The use of Embodiment 41, wherein the oral solid dosage form is a tablet, a capsule, a pill, or a plurality of granules.

Embodiment 43. The use of Embodiment 40, wherein the oral dosage form is an oral solution or an oral suspension.

EXAMPLES

The methods of treatment or prevention and uses described herein are now further detailed with reference to the following examples. These examples are provided for the purpose of illustration only and the embodiments described herein should in no way be construed as being limited to these examples. Rather, the embodiments should be construed to encompass any and all variations which become evident as a result of the teaching provided herein.

Example 1

Evaluation of Mitochondrial Pyruvate Carrier (MPC) Inhibitory Activity of MIN-102

BRET-Assay

To monitor the activity of the MPC in real time, i.e., the MPC inhibitory activity ($IC_{50}$), a BRET assay was used transfecting the appropriate chimeric proteins in HEK cells as described in Compan et al., *Molecular Cell* 59:491-501 (2015).

The MPC is a heterodimer composed of two subunits, MPC1 and MPC2. MPC1 and MPC2 interact to form an active carrier. In the assay, MPC2 was fused to Rluc8 (Donor) and MPC1 to Venus (Acceptor). These chimeric proteins were stably expressed in HEK cells. BRET activity was measured following addition of coelenterazine in the culture medium. Coelenterazine enters into cells and in contact with luciferase Rluc8 emits light, which activates the emission of fluorescence by the Acceptor, provided the distance between the Donor and Acceptor is <100 nm. If the distance between Donor and Acceptor is >100 nm, no BRET activity is measured. The level of BRET activity reflects a change in the conformation of the MPC: it is high when the carrier is in a closed conformation, low when the carrier is at rest and intermediary when it transports pyruvate. In this case, the BRET activity is the mean value between the BRET value when the carrier is at rest (Maximal distance between Donor and Acceptor) and the BRET value when it is closed (Shortest distance between Donor and Acceptor)

A wide range of concentrations of each tested compound was used from 1 nM to 100 µM. The dose response curves of the tested compounds MIN-102 and pioglitazone are shown in FIG. 1.

The BRET activity measured for each tested compound was compared with the BRET activity obtained when HEK cells are incubated in PBS (resting state) and in PBS+ pyruvate, which corresponds to the intermediary value between the resting state and the close state (maximal closure obtained with UK5099). Table 1 below provides the $IC_{50}$ values for the tested compounds MIN-102, pioglitazone, rosiglitazone and UK5099 obtained in the BRET assay described above.

TABLE 1

| Compound | IC50 |
|---|---|
| MIN-102 | 4.1 µM |
| Rosiglitazone | 2 µM |
| UK5099 | 17 nM |
| Pioglitazone | >100 µM |

MIN-102 inhibits the MPC activity in the BRET assay with an $IC_{50}$ value of 4.1 µM. The activity of MIN-102 is slightly lower than the activity of rosiglitazone ($IC_{50}$=2 µM). Accordingly, MIN-102 is a MPC inhibitor with an $IC_{50}$ of 4.1 µM, whereas pioglitazone does not inhibit MPC having an $IC_{50}$ value more than 100 µM.

Mitochondrial Respiration

Figure 2A:
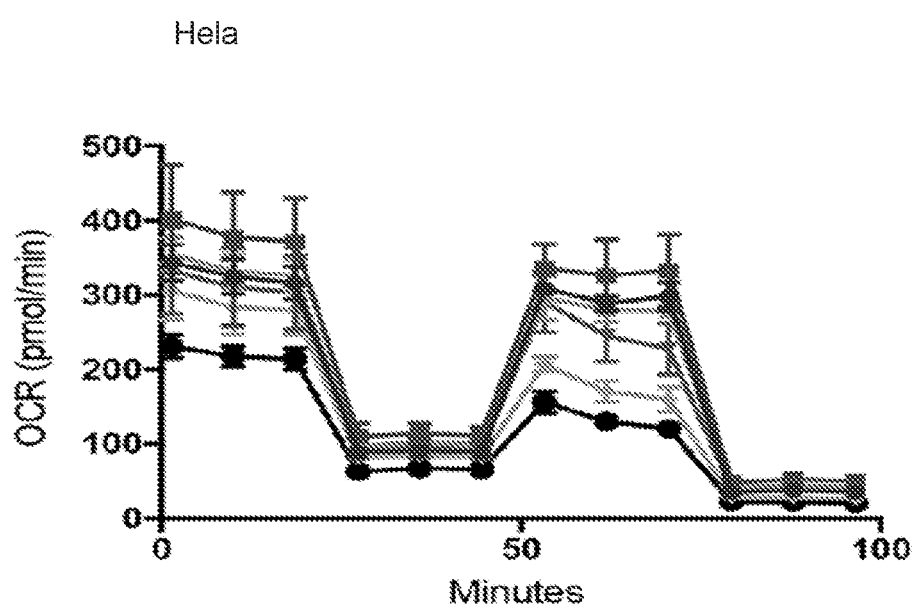
FIG. 2A is a line graph showing the effect of MIN-102 on OCR in Hela cells.
Figure 2B:
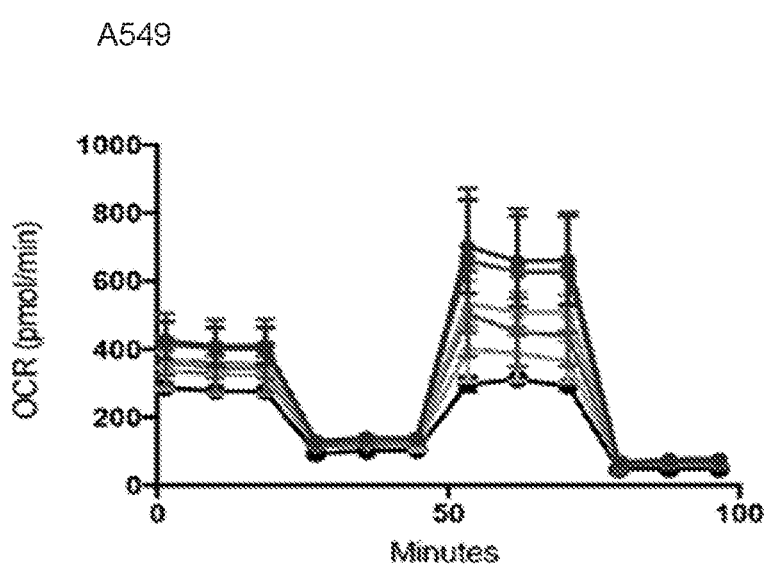
FIG. 2B is a line graph showing the effect of MIN-102 on OCR in A549 cells.

To determine whether MIN-102 has any effect on pyruvate-mediated mitochondrial respiration, the extracellular flux analyzer Seahorse was used as described in Compan et al. Seahorse experiments were performed in the following cell lines: HeLa (Cervix cancer cells), A549 (lung cancer cells), wild type MDA MB 231, and MDA MB 231 in which MPC2 has been deleted, leading to inactivation of the MPC (MDA MB231 KO). MDA MB231 cells are epithelial breast cancer cells. Cells were incubated with increasing concentrations of the compounds for one hour at 37° C. before oxygen consumption rate (OCR) measurements. The Seahorse analyzer allowed to measure basal and maximal respiration measured upon depolarization with 1 µM CCCP. The results are shown in FIG. 2 and FIG. 3.

Effects of MIN-102 on oxygen consumption rates (OCR) in HeLa cells (FIG. 2A) and A549 cells (FIG. 2B) in a representative experiment of n=3. OCR values are expressed as ratios of OCR in the presence of different concentrations of compounds over the OCR in PBS alone. $IC_{50}$ in both cells lines was around 5 µM.

Figure 3A:
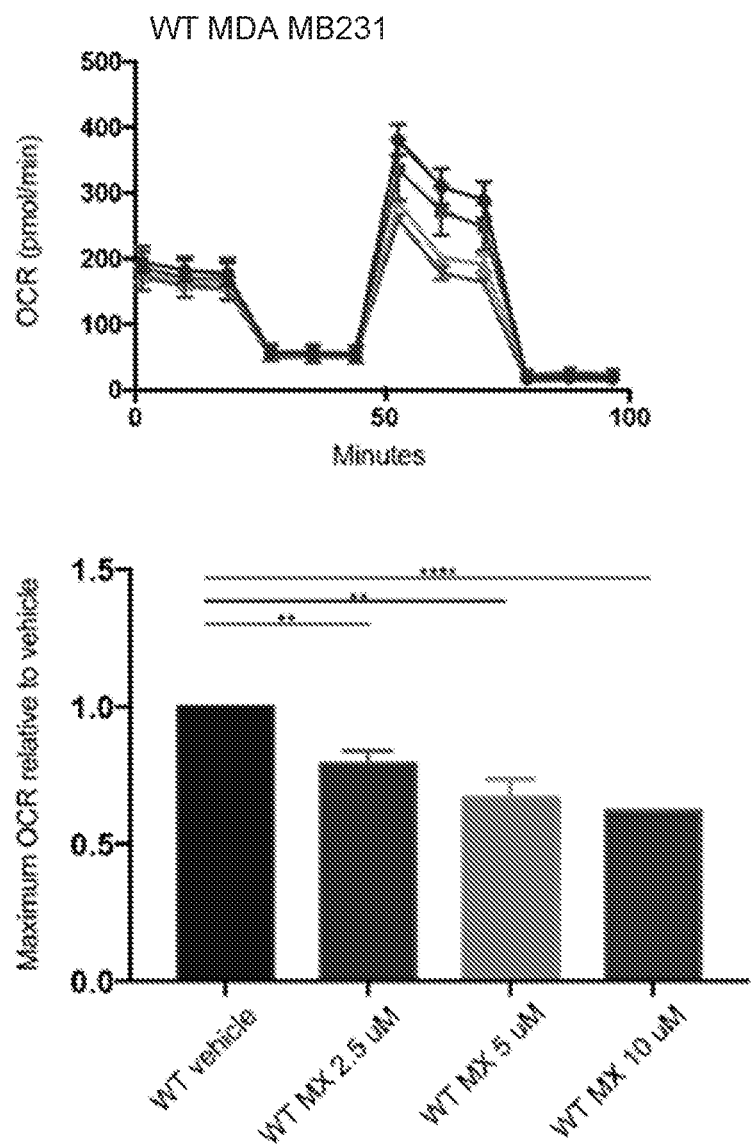
FIG. 3A is a line graph showing the effect of MIN-102 on OCR in wild type MDS MB231 cells.
Figure 3B:
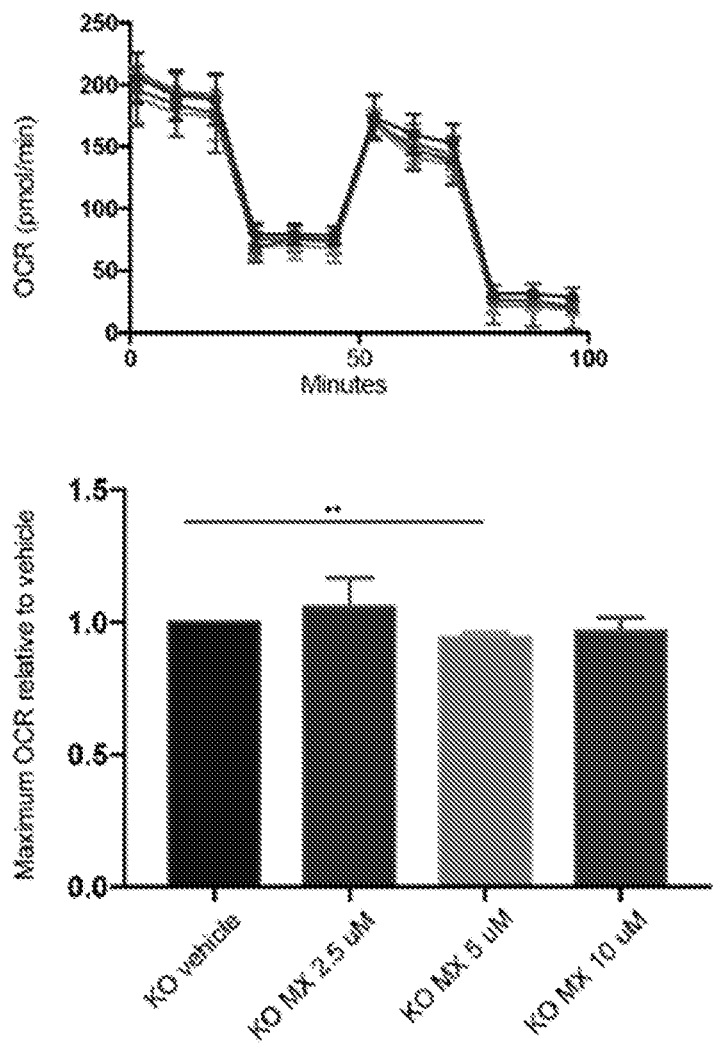
FIG. 3B is a line graph showing the effect of MIN-102 on OCR in MDS MB231 KO cells.

FIG. 3 shows the effects of MIN-102 on wild type MDA MB231 cells (FIG. 3A) and MDA MB231 KO cells (FIG. 3B). The KO cells have been deleted of the MPC2 gene and therefore they display no MPC activity. The top panel shows a representative experiment of either wild type (WT) or KO cell lines. The bottom panel shows the mean values of maximal OCR in 3 different experiments. OCR values are expressed as ratios of OCR in the presence of different concentrations of the tested compound over the OCR in PBS alone.

CONCLUSION

MIN-102 inhibits the MPC activity with an $IC_{50}$ value of 4.1 µM and inhibits oxygen consumption in a MPC dependent manner. Indeed, MIN-102 does not inhibit oxygen consumption when the activity of the MPC has been genetically deleted, supporting that MIN-102 is a specific inhibitor of MPC. The inhibitory activity of MIN-102 on the MPC is low compared to the activity of UK5099 ($IC_{50}$=17 nM), a potent chemical compound inhibitor of MPC, and slightly lower but in the same range than the activity of rosiglitazone ($IC_{50}$=2 Compounds of the Disclosure, such as MIN-102, are significantly more potent than pioglitazone.

Based on the results, it can be concluded that Compounds of the Disclosure, such as MIN-102, would offer a much better treatment than pioglitazone for diseases in which the energetic requirements are modified.

Example 2

MIN-102 Significantly Increases Adiponectin Levels in Plasma

Mitochondrial function is linked to adiponectin synthesis in adipocytes, and mitochondrial dysfunction in adipose tissue may explain decreased plasma adiponectin levels in obesity. Impaired mitochondrial function activates a series of mechanisms involving ER stress, JNK, and ATF3 to decrease adiponectin synthesis. See, Eun Hee Koh et al., *Diabetes* 56(12):2973-2981 (2007). In addition, hepatic adiponectin receptors are diminished in NASH patients and adiponectin knockout mice develop a more extensive liver fibrosis compared with wild-type animals, whereas adenovirus-mediated overexpression of adiponectin ameliorates liver damage in wild-type mice. (See, e.g., Kamada et al., *Gastroenterology* 125:1796-1807 (2003)).

Evaluation of the effect of Compounds of the Disclosure on adiponectin was performed in Sprague Dawley rats. The rats were treated for 7 days with repeated doses of MIN-102 at 54 mg/Kg/day. Plasma were obtained at 1 h after the last MIN-102 administration. Adiponectin levels were measured by ELISA. Results were represented as mean+standard error of the mean of n=8. Data were analyzed by Kruskal-Wallis followed by the Dunn post-hoc test versus the vehicle group (****, $p<0.0001$).

Figure 4:
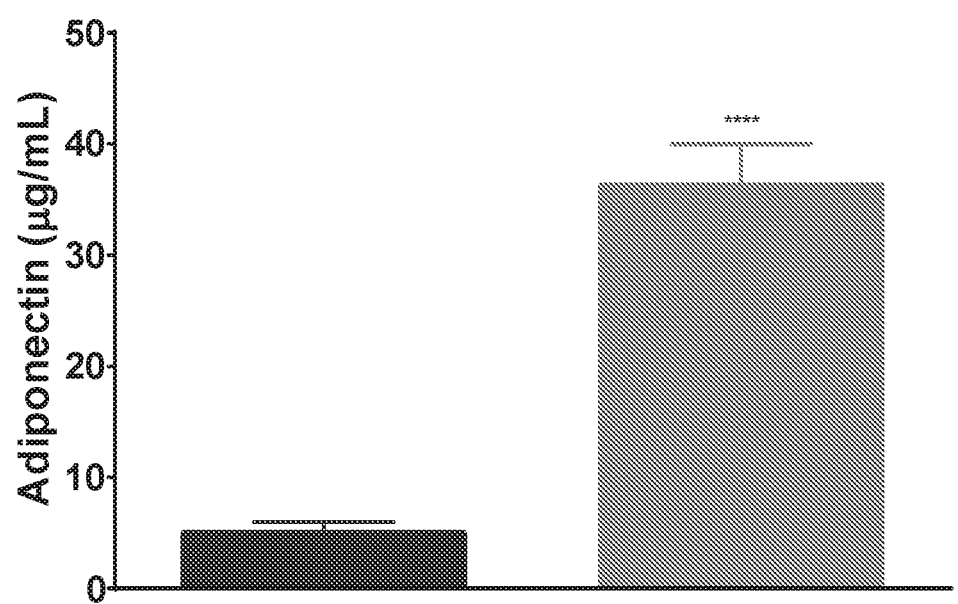
FIG. 4 represents a comparison of adiponectin levels in Sprague Dawley rats after treatment with MIN-102.

As shown in FIG. 4, MIN-102 treatment significantly increased the levels of adiponectin. Accordingly, it can be concluded based on these data that because MIN-102 treatment significantly increases the levels of adiponectin, MIN-102 could also correct the deficiency of adiponectin observed in patients suffering from a mitochondrial disease, such as in LHON patients. See, Abou-Samra et al., *Skeletal Muscle* 5:25 (2015).

Example 3

In Vivo Model of Duchenne

Compounds of the Disclosure can be tested for their efficacy in treating Duchenne muscular dystrophy (DMD) as follows.

Dystrophin-deficient mice: The mdx mouse is a naturally occurring animal model for DMD and it was discovered in the early 1980s in a colony of C57BL/10ScSn mice due to elevated serum creatine kinase (CK) and histological evidence of myopathy (McGreevy et al., *Disease Models & Mechanisms* 8:195-213 (2015)). The mutation in the mdx mouse is a nonsense point mutation (C-to-T transition) in exon 23 that aborted full-length dystrophin expression.

Between 3 to 6 weeks, mdx muscle undergoes startling necrosis. Subsequently, the majority of skeletal muscle enters a relatively stable phase owing to robust regeneration. mdx limb muscles often become hypertrophic during this phase. Severe dystrophic phenotypes, such as muscle wasting, scoliosis and heart failure, do not occur until mice are 15 months or older (Bostick et al., *Circulation Research Han.* 4/18:121-130 (2008); Bostick et al., *Molecular Therapy* 17(2):253-261 (2009)).

On this test, C57BL/10ScSn mdx mice are treated either with a vehicle or a Compound of the Disclosure, such as 5-[[4-[2-[5-(R)-(1-hydroxyethyl)pyridin-2-yl]ethoxy]phenyl]methyl]-1,3-thiazolidine-2,4-dione hydrochloride (MIN-102). These animals are maintained under a standard laboratory chow and housed at a constant temperature with a fixed light-dark cycle. At the end of the experiments, mice are sacrificed by cervical dislocation. Blood samples are saved. Pairs of tibialis anterior (TA) muscles or inguinal fat pads are weighed, frozen in liquid nitrogen, and stored at −80° C. for subsequent analyses. For some experiments dealing with evaluation of muscle injury, additional muscles can be sampled.

In vivo studies of global force or resistance: Mice are submitted to three main tests:

Wire test: Animals are suspended by their forelimbs from a 1.5 mm-thick, 60 cm-long metallic wire at 45 cm above soft ground. The time (seconds) until the mouse completely releases its grasp and fall down is recorded. Three trials are performed per session, with a 30-s recovery period between trials. The maximum time per trial is set to 180 seconds. For each mouse, the scores of the three trials are averaged (Zanou et al., *J. Physiol.* 593.17:3849-3863 (2010)).

Grip test: The grip strength test measures the muscle strength of forelimb or of combined fore- and hindlimb muscles. Limb strength is recorded using a grid connected to a sensor (Panlab-Bioseb, Vitrolles, France). The mice are gently laid on the top of the grid so that their front paws (forelimb test) or both fore and hind paws (combined test) can grip the grid. Then, mice are pulled back steadily until the grip is released down the complete length of the grid. Each test is repeated three times at an interval of 20 min. Results are presented as the mean of the two highest values of force recorded, related to body weight.

Quantification of muscle damage markers in plasma: Plasma creatine kinase (CK) and lactate dehydrogenase (LDH) activities can be quantified to evaluate skeletal muscle damage as injured muscles release CK and LDH into the bloodstream at high levels. Kits are based on colorimetric methods (Gentaur, Kampenhout, Belgium). CK and LDH activities are expressed as IU/L.

Example 4

Analysis of Mitochondrial Respiration In Vitro

The effect of Compounds of the Disclosure on relevant cells such as iPSC derived neurons or fibroblasts from mitochondrial DNA diseases, including LHON, KSS, MELAS, Pearson, Leigh and MILS, can be tested for oxygen consumption.

Analysis of mitochondrial respiratory potential is performed using a flux analyzer (Seahorse XF$^e$24 Extracellular Flux Analyzer; Seahorse Bioscience, North Billerica, Mass., USA) with a Seahorse XF Cell Mito Stress Test Kit (Seahorse Bioscience) according to the manufacturer's instructions. Basal respiration and ATP production are calculated to evaluate mitochondrial respiratory function according to the manufacturer's instructions. After the measurement, cells are harvested to count the cell number, and each plotted value is normalized relative to the number of cells used.

Example 5

In Vitro Studies in Fibroblasts

Fibroblasts are the preferred cell model to study ex vivo cellular alterations of patients in a first line, because they grow rapidly, are easy to manipulate and require a single extraction, which is a good element to draw a first scenario of which parameters of mitochondrial function recover by the treatment with a Compound of the Disclosure, such as MIN-102. Fibroblasts from patients suffering from Rett syndrome, Dominant Optic Atrophy (DOA), Autosomal Dominant Optic Atrophy (ADOA), such as OPA-1 mutation disease, and Complex I deficiency (NADH dehydrogenase (NADH-CoQ reductase) deficiency), including NDUFS1 deficiency, can be used for the following studies:

1. Analysis of Mitochondrial Function and Dynamics Proteins:

Two groups of proteins can be studied: on one hand, the proteins that have been described under the transcriptional regulation of PPAR gamma, and on the other hand proteins that indicate mitochondrial function and dynamics, such as mitofusins, dynamines, ATP synthase, and IF1. This analysis can be performed by Western Blot of fibroblast cultures before and after exposure to the Compound of the Disclosure, such as MIN-102.

2. Study of the Cellular Energy State:

The following parameters can be studied to analyze the mitochondrial respiratory capacity in fibroblasts:

Measurement of cellular ATP concentration (commercial kit ATP Bioluminiscence Assay Kit CLS II, Roche) and oxygen consumption and CO2 release by real-time plate respirometry assay (Seahorse XF technology, Agilent).

These parameters can provide complete picture of mitochondrial energy activity, before and after exposure to a test compound, such as MIN-102.

3. Study of the Presence of Reactive Oxygen Species (ROS) in Cells in Culture:

Based on the literature (see, e.g., Signorini et al., *Oxidative Medicine and Cellular Longevity Volume* 2014, Article ID 195935, 10 pages (2014)), the presence of ROS is being associated with mitochondrial dysfunction and it is measured in models of Rett syndrome. The effect of a Compound of the disclosure on the concentration of ROS can be measured by the use of specific probes, such as MitoSOX, H2DCFDA and JM1, which will be analyzed by fluorescence microscopy or flow cytometry. In the presence of ROS, cellular antioxidant systems will be analyzed by Western Blot, evaluating the expression of the MnSOD, GPX and GSH proteins.

4. Visualization of the Network and Mitochondrial Ultrastructure:

The effect of a Compound of the Disclosure on the state of the mitochondrial network can be analyzed by means of the incubation with the MitoTracker fluorescent probe and the analysis of the length, arrangement and density of mitochondrial crests by visualizing the mitochondrial ultrastructure by electron microscopy.

Example 6

In Vitro Studies in Lymphoplasts

Lymphoblasts from primary and secondary mitochondrial disorders, such as Friedreich's ataxia and Huntington, can be studied to observe the potential reversion of the mitochondrial dysfunction by treatment with a Compound of the Disclosure, such as MIN-102. Lymphoblast cell cultures are established by immortalization of the cells from peripheral blood samples from patient samples by Epstein Barr virus (EBV) serving as rapidly growing and permanent cultures for studies.

Mitochondrial impairment can be tested by measuring ATP levels in a glucose-free galactose medium which forces generation of ATP through OXPHOS The results from this study can be compared with those obtained in glucose-free media. In addition, the degree of complex I driven ATP synthesis can be monitored in decreased significantly by lymphoblast cultures.

Example 7

Effects of MIN-102 in the Methionine Choline Deficient Diet Fed Mice

The preventive effects of MIN-102 was evaluated in a 7-week Methionine Choline Deficient (MCD) diet NASH mouse model (Verdelho Machado et al.). After the acclimation period, C57BL6/J male mice (n=20) were weighed and randomized into 2 homogenous treatment groups based on body weight (n=10/group), put on a MCD diet, and treated BID orally with vehicle or MIN-102 for 7 weeks.

MIN-102 was dosed 62.5 mg/kg BID orally by gavage.

When C57BL6/J mice are fed a MCD diet, they rapidly develop liver steatosis, inflammation and fibrosis with concomitant increase in plasma alanine transaminase (ALT)/aspartate aminotransferase (AST) levels.

Material and Methods

After the acclimation period, C57BL6/J male mice (n=20) were weighed and randomized into 2 homogenous treatment groups based on body weight (n=10/group), put on a MCD diet, and treated BID orally with a vehicle or MIN-102 (125 mg/Kg/day) for 7 weeks. Body weight was measured 3 times/week until the end of the experimental phase.

At 7 weeks of diet/treatment, mice were weighed and treated at ~08:00 am in the morning, then bled (maximal volume/EDTA) at ~1:00 pm. Plasma was then immediately isolated and stored at −80° C. prior to assay plasma ALT and AST. The plasma volume left over was stored at −80° C. for eventual additional analysis.

After blood collection, the mice were sacrificed by cervical dislocation under isoflurane anesthesia and exsanguinated with sterile saline.

Results

As expected, the mice under MCD diet showed substantial body weight loss. The mice treated with MIN-102 showed a less severe decline in body weight loss, from day 14 to day 50, leading to significant differences between day 30 and day 50.

As also expected, MCD diet resulted in very high ALT and AST plasma levels (mean values of 480 U/L and 455 U/L, respectively) at the end of the treatment. Treatment with MIN-102 substantially reduced both plasma ALT and AST levels by 78% and 55%, respectively (both $p<0.01$ vs. vehicle).

The mice treated with MIN-102 did not show a change in hepatic cholesterol levels, but showed a dramatic reduction in hepatic triglycerides levels by 92% ($p<0.001$ vs. vehicle).

Histology analysis was performed (oil red O, H&E and Sirius Red staining) for NAFLD scoring system (NAS) for liver steatosis, inflammation, fibrosis and hepatocyte ballooning.

Mean NAS group scores were 3.40±0.3 and 0.44±01 in vehicle and MIN-102, respectively ($p<0.001$ vs. vehicle). The strong reduction in the NAS score was related to a blunted steatosis score ($p<0.001$ vs. vehicle), which was confirmed by an extremely low oil red o staining % as compared with vehicle ($p<0.001$), and a total disappearance of inflammation.

In conclusion, the present study demonstrates a strong reduction in liver steatosis and inflammation in MCD mice treated with MIN-102.

Having now fully described this disclosure, it will be understood by those of ordinary skill in the art that the same can be performed within a wide and equivalent range of conditions, formulations, and other parameters without affecting the scope of the invention or any embodiment thereof.

Other embodiments of the disclosure will be apparent to those skilled in the art from consideration of the specification and practice of the invention disclosed herein. It is intended that the specification and examples be considered exemplary only, with a true scope and spirit of the invention being indicated by the following claims.

All patents, patent applications, and publications cited herein are fully incorporated by reference herein in their entirety.

What is claimed is:

1. A method of treating a mitochondrial disease, comprising administering to a subject in need thereof a compound of formula (1)

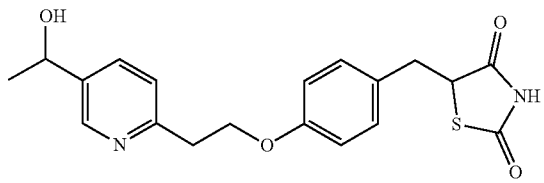

or a pharmaceutically acceptable salt thereof, in an amount effective to treat said mitochondrial disease, wherein said mitochondrial disease is selected from the group consisting of Rett syndrome, Leigh's syndrome, autosomal dominant optic atrophy (ADOA), Complex I deficiency, Leber's hereditary optic neuropathy (LHON), mitochondrial encephalomyopathy with lactic acidosis and stroke-like episodes (MELAS), and NDUFS1 deficiency.

2. The method according to claim 1, wherein the mitochondrial disease is Rett syndrome.

3. The method according to claim 1, wherein the mitochondrial disease is Leigh's syndrome.

4. The method according to claim 1, wherein the mitochondrial disease is autosomal dominant optic atrophy (ADOA).

5. The method according to claim 4, wherein the ADOA is OPA-1 mutation disease.

6. The method according to claim 1, wherein the compound of formula (1) is selected from the group consisting of:
   compound (2): (R)-5-[[4-[2-[5-(R)-(1-hydroxyethyl)pyridin-2-yl]ethoxy]-phenyl]methyl]-1,3-thiazolidine-2,4-dione;
   compound (3): (R)-5-[[4-[2-[5-(S)-(1-hydroxyethyl)pyridin-2-yl]ethoxy]-phenyl]methyl]-1,3-thiazolidine-2,4-dione;
   compound (4): (S)-5-[[4-[2-[5-(R)-(1-hydroxyethyl)pyridin-2-yl]ethoxy]-phenyl]methyl]-1,3-thiazolidine-2,4-dione; and
   compound (5): (S)-5-[[4-[2-[5-(S)-(1-hydroxyethyl)pyridin-2-yl]ethoxy]-phenyl]methyl]-1,3-thiazolidine-2,4-dione;
   or a pharmaceutically acceptable salt thereof.

7. The method according to claim 6, comprising administering a mixture of two or more of compounds selected from the group consisting of compound (2), compound (3), compound (4), and compound (5), or a pharmaceutically acceptable salt thereof.

8. The method according to claim 7, wherein the mixture comprises:
   (a) the compound (2) and the compound (3);
   (b) the compound (4) and the compound (5);
   (c) the compound (2) and the compound (4); or
   (d) the compound (3) and the compound (5),
   or a pharmaceutically acceptable salt thereof.

9. The method according to claim 7, comprising administering a mixture comprising each compound (2), compound (3), compound (4), and compound (5) in an amount of 25%±5% w/w.

10. The method according to claim 1, further comprising administering another therapeutic agent.

11. The method according to claim 10, wherein the compound of formula (1), or a pharmaceutically acceptable salt thereof, and said another therapeutic agent are provided in combination.

12. The method according to claim 1, wherein no more than 1% of the total number of hydrogen atoms per mole of the compound of formula (1) are in the form of the $^2$H isotope.

13. The method according to claim 1, wherein the compound of formula (1), or a pharmaceutically acceptable salt thereof, is administered to the subject in an oral, intraoral, topical, epicutaneous, subcutaneous, transdermal, intramuscular, parenteral, ocular, rectal, vaginal, inhalation, buccal, sublingual, or intranasal dosage form.

14. The method according to claim 13, wherein the dosage form is an oral dosage form.

15. The method according to claim 14, wherein the oral dosage form is solid.

16. The method according to claim 15, wherein the oral solid dosage form is a tablet, a capsule, a pill, or a plurality of granules.

17. The method according to claim 14, wherein the oral dosage form is an oral solution or an oral suspension.

18. The method of claim 1, wherein the subject is a child or a teen.

* * * * *